(12) United States Patent
Scheffler et al.

(10) Patent No.: US 9,103,819 B2
(45) Date of Patent: Aug. 11, 2015

(54) PERIPHERAL ZONE TUMOR CELLS, METHODS FOR THEIR PREPARATION AND USE

(75) Inventors: Björn Scheffler, Remagen-Oberwinter (DE); Matthias Simon, Bonn (DE); Oliver Brüstle, Bonn (DE); Ulrich Johannes Herrlinger, Bonn (DE); Martin Glas, Bonn (DE)

(73) Assignee: Rheinische Friedrich-Wilhelms-Universität Bonn, Bonn (DE)

( * ) Notice: Subject to any disclaimer, the term of this patent is extended or adjusted under 35 U.S.C. 154(b) by 989 days.

(21) Appl. No.: 12/867,442

(22) PCT Filed: Sep. 9, 2009

(86) PCT No.: PCT/EP2009/006547
§ 371 (c)(1),
(2), (4) Date: Nov. 9, 2010

(87) PCT Pub. No.: WO2010/028820
PCT Pub. Date: Mar. 18, 2010

(65) Prior Publication Data
US 2011/0052642 A1   Mar. 3, 2011

Related U.S. Application Data

(60) Provisional application No. 61/191,640, filed on Sep. 10, 2008.

(51) Int. Cl.
*G01N 33/574* (2006.01)
*C12N 5/09* (2010.01)
*G01N 33/50* (2006.01)
*C12N 5/079* (2010.01)
*A61P 35/00* (2006.01)

(52) U.S. Cl.
CPC .......... *G01N 33/5011* (2013.01); *C12N 5/0618* (2013.01); *C12N 5/0622* (2013.01); *C12N 5/0693* (2013.01); *G01N 33/502* (2013.01); *G01N 33/5017* (2013.01); *G01N 33/5058* (2013.01); *G01N 33/574* (2013.01); *G01N 2333/705* (2013.01); *G01N 2333/70596* (2013.01); *G01N 2500/10* (2013.01)

(58) Field of Classification Search
None
See application file for complete search history.

(56) References Cited

U.S. PATENT DOCUMENTS 5,891,432 A * 4/1999 Hoo .......................... 424/93.21
2004/0072345 A1 * 4/2004 Altaba et al. ................. 435/368
2007/0037224 A1 * 2/2007 Hamer et al. ................. 435/7.21
2010/0135975 A1 * 6/2010 Yu et al. ...................... 424/93.71

FOREIGN PATENT DOCUMENTS

CA       2 447 400 A1      3/2005
WO    WO2007/062138    *  5/2007
WO    WO 2007/134274 A2  11/2007
WO    WO2008/033393    *  3/2008
WO    WO 2007/134274 A3  10/2008

OTHER PUBLICATIONS

Gilbert and Ross, Journal of Cellular Biochemistry, 2009, vol. 108, pp. 1031-1038.*
Visvader and Lindeman, Nature Reviews Cancer, 2008, vol. 8, pp. 755-767.*
Fujita et al, Cancer Research, 2009, vol. 69, pp. 1587-6682.*
Balenci et al (Cancer Research, 2006, vol. 66, pp. 9074-9082).*
Abstract of Park et al (Society for Neuroscience, 2008 Annual Meeting, Nov. 11, 2008, Abstract 654.21/DD2).*
Yang and Wechsler-Reya (Cancer Cell, 2007, vol. 11, pp. 3-5).*
Gross et al (Journal of Cancer Research and Clinical Oncology, 2006, vol. 132, pp. 589-599).*
Vallera et al (Journal of the National Cancer Institute, 2002, vol. 94, pp. 597-606).*
Parajuli et al (Neurosurgery, 2004, vol. 55, pp. 1194-1204).*
Mohanam et al (Frontiers in Bioscience, 1999, vol. 178, pp. d178-d187).*
Knappe et al (Acta Neuropathologia, 2003, vol. 106, pp. 471-478).*
Lee et al (Leukemia Research, 2001, vol. 25, pp. 757-767).*
Yamamoto et al (Cancer Research, 1994, vol. 54, pp. 5016-5020).*
Pedersen et al (Cancer Research, 1994, vol. 54, pp. 4671-4675).*
Al-Moundhri et al (World Journal of Gastroenterology, Jun. 28, 2008, vol. 14, pp. 3879-3883).*
Mochimaru et al (Investigative Ophthalmology and Visual Science, 2007, vol. 48, pp. 4795-4801).*
Pan et al (Gene Therapy, 2005, vol. 12, pp. 742-750).*
Kaplan et al (Vaccine, 2006, vol. 24, pp. 6994-7002).*
Zeppernick et al (Clinical Cancer Research, Jan. 1, 2008, vol. 14, pp. 123-129).*
Jenny et al (Journal of Pathology, 2006, vol. 209, pp. 34-43).*
Dahlstrand et al (Cancer Research, 1992, vol. 52, pp. 5334-5341).*
R & D Systems, Inc. product insert for "Quantikine.TM. ELISA, Human VEGF R2/KDR Immunoassay" package insert (downloaded from the Web on Jan. 20, 2014).*
Wheeler (Salud p'ublica de M'exico, 1997, vol. 39, pp. 283-287).*
Efferson et al (Anticancer research, 2005, vol. 25, pp. 715-724).*
Bachmann et al (Journal of Immunology, 2005, vol. 175, pp. 4677-4685).*
Opel et al (Cancer Research, Aug. 1, 2008, vol. 68, pp. 6271-6280).*
Potapova et al (Molecular Cancer Therapeutics, 2006, vol. 5, pp. 1280-1289).*

(Continued)

*Primary Examiner* — Karen Canella
(74) *Attorney, Agent, or Firm* — Clark & Elbing LLP

(57) ABSTRACT

The present invention relates to a tumor cell of the peripheral zone of a tumor and methods of providing such a tumor cell. Further provided is a method for identifying a molecular marker diagnostic for an infiltrative cancer, an antibody, which specifically binds to such molecular marker, a method for identifying a therapeutic compound effective against a metastatic/infiltrative cancer disease and the use of a tumor cell according to the invention.

24 Claims, 15 Drawing Sheets
(12 of 15 Drawing Sheet(s) Filed in Color)

(56) References Cited

OTHER PUBLICATIONS

Farthmann et al (Radiology and Oncology, 2004, vol. 38, pp. 111-119).*
Nister et al (The Journal of Biological chemistry, 1991, vol. 266, pp. 16755-16763).*
Li et al (Clinical Cancer Research, Aug. 1, 2008, vol. 14, pp. 4758-4766).*
Bachtiary et al., "Gene Expression Profiling in Cervical Cancer: An Exploration of Intratumor Heterogeneity," *Clin. Cancer Res.* 12(19):5632-5640 (2006).
Beier et al., "CD133(+) and CD133(−) Glioblastoma-Derived Cancer Stem Cells Show Differential Growth Characteristics and Molecular Profiles," *Cancer Res.* 67(9):4010-4015 (2007).
Bidlingmaier et al., "The Utility and Limitations of Glycosylated Human CD133 Epitopes in Defining Cancer Stem Cells," *J. Mol. Med.* 86:1025-1032 (2008).
Gutova et al., "Identification of uPAR-positive Chemoresistant Cells in Small Cell Lung Cancer," *PLoS ONE* 2(2):e243 (2007).
International Search Report for International Application No. PCT/EP2009/006547, mailed Sep. 4, 2010.
Kitadai et al., "Multiparametric in Situ Messenger RNA Hybridization Analysis to Detect Metastasis-related Genes in Surgical Specimens of Human Colon Carcinomas," *Clin. Cancer Res.* 1:1095-1102 (1995).
McArthur, "Molecularly Targeted Treatment for Dermatofibrosarcoma Protuberans," *Seminars in Oncology* 31(2) Supp. 6:30-36 (2004).
Mentlein et al., "Functional Significance of Vascular Endothelial Growth Factor Receptor Expression on Human Glioma Cells," *Journal of Neuro-Oncology* 67:9-18 (2004).
Nakamura et al., "Zonal Heterogeneity for Gene Expression in Human Pancreatic Carcinoma," *Cancer Res.* 67(16):7597-7604 (2007).
Owonikoko et al., "Intratumoral Genetic Heterogeneity in Barrett Adenocarcinoma" *Am. J. Clin. Pathol.* 117:558-566 (2002).
Piccirillo et al., "Distinct Pools of Cancer Stem-like Cells Coexist within Human Gliobastomas and Display Different Tumorigenicity and Independent Genomic Evolution," *Oncogene* 28:1807-1811 (2009).
Schrot et al., "Organotypic Distribution of Stem Cell Markers in Formalin-Fixed Brain Harboring Glioblastoma Multiforme," *J. Neurooncol.* 85:149-157 (2007).
Singh et al., "Identification of Human Brain Tumour Initiating Cells," *Nature* 432:396-401 (2004).
Written Opinion for International Patent Application No. PCT/EP2009/006547, mailed Sep. 4, 2010.
Notification Concerning Transmittal of International Preliminary Report on Patentability, mailed Mar. 24, 2011.

* cited by examiner

Figure 3
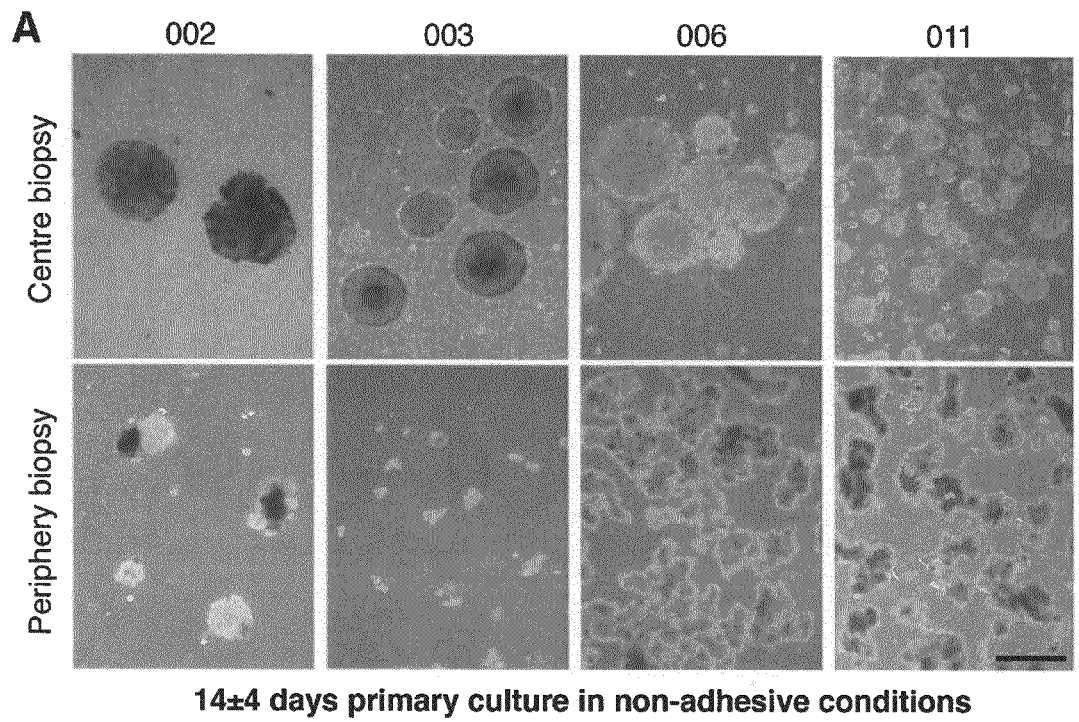
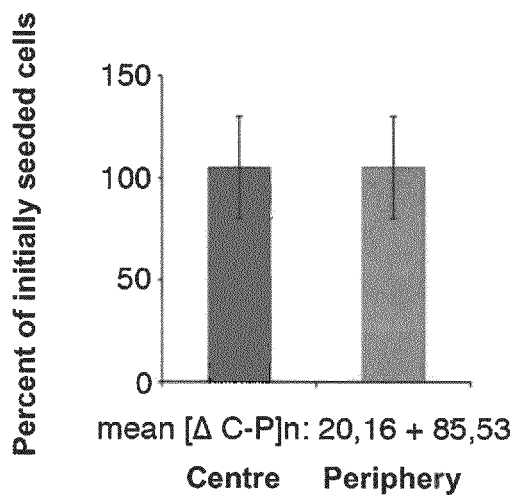

Figure 5
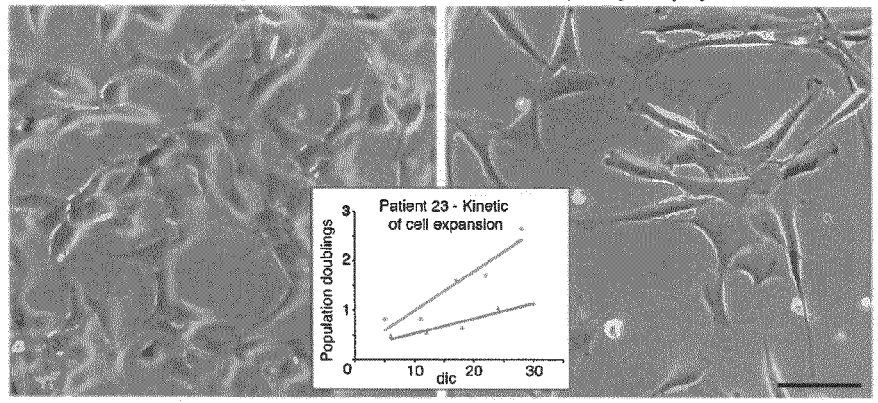
Analysis of growth kinetics in vitro between passages 5 and 10
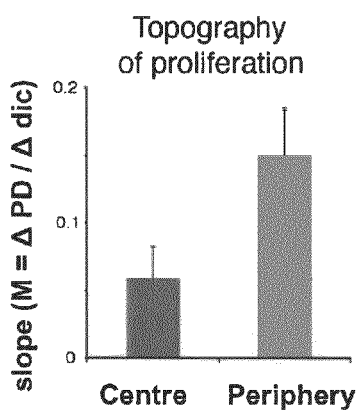
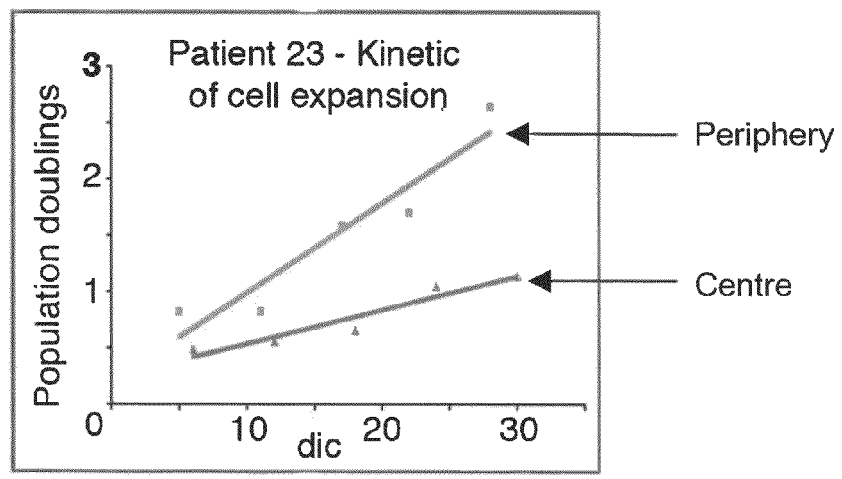

Figure 9

| Patient | Diagnosis | Sex | Age | Histology of biopsy specimen | |
|---|---|---|---|---|---|
| | | | | Center | Periphery |
| 001 | New | m | 65 | GBM/INF | INF |
| 002 | New | f | 71 | GBM | INF/GBM |
| 003 | New | f | 67 | GBM | INF |
| 004 | New | f | 71 | GBM | INF |
| 005 | New | m | 55 | GBM | INF |
| 006 | New | f | 46 | GBM | INF |
| 007 | New | m | 55 | GBM | INF |
| 008 | New | m | 47 | GBM | INF |
| 009 | New (secondary) | m | 60 | GBM/INF | INF |
| 010 | New | m | 77 | GBM/INF | INF/GBM |
| 011 | New | m | 66 | GBM | INF |
| 012 | New (secondary) | f | 27 | GBM | INF |
| 013 | New | m | 57 | GBM | INF |
| 015 | New | f | 42 | GBM | GBM |
| 016 | New | f | 43 | GBM/INF | INF/GBM |
| 017 | New | f | 67 | INF/GBM | INF |
| 018 | New | m | 43 | GBM | INF |
| 020 | New | m | 52 | GBM | INF |
| 021 | New | m | 78 | GBM | INF/GBM |
| 023 | New | f | 79 | GBM | INF |
| 025 | New | m | 70 | GBM | INF |
| 026 | Relapse | f | 63 | GBM | INF |
| 029 | New | m | 37 | GBM/INF | INF |
| 030 | New | m | 77 | GBM | INF |
| 031 | Relapse | m | 76 | GBM | INF |
| 032 | New | m | 73 | GBM | INF |
| 033 | New (secondary) | m | 32 | GBM | INF |
| 035 | New | f | 75 | GBM | INF/GBM |
| 037 | New | f | 59 | GBM | INF |
| 046 | New | m | 76 | GBM | INF |

Age: Patient age at surgery in years

INF: Histological hallmarks of an infiltration zone

GBM: Histological hallmarks of a Glioblastoma multiforme

GBM/INF: sample with GBM characteristics and a small part of INF

INF/GBM: sample with INF charactzeristics and a small part of GBM

Figure 11
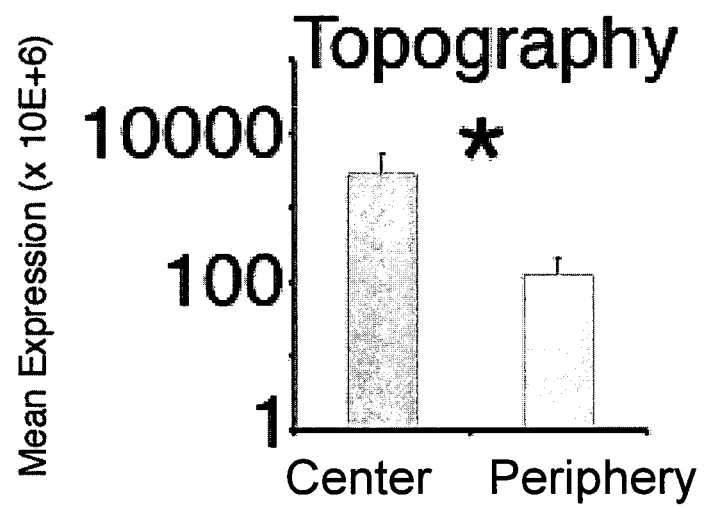
VEGFR-2
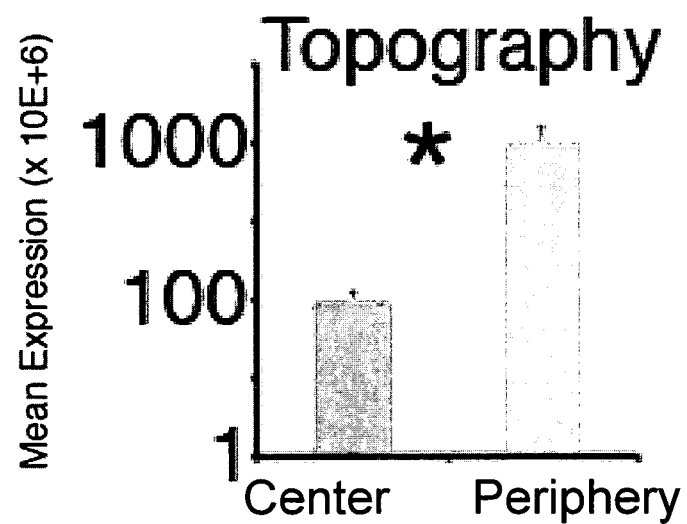
PDGFR-B

Figure 13

| mRNA targets | Oligonucleotides (custom-made) | product size (bp) |
| --- | --- | --- |
| CD44 | Fwd: CCAGCTAAGGACATTTCCCA (SEQ ID NO: 5)<br>Rev: ACTAGTACACCCCAACCCCC (SEQ ID NO: 6) | 134 |
| L1CAM | Fwd: GACTACGAGATCCACTTGTTTAAGGA (SEQ ID NO: 7)<br>Rev: CTCACAAAGCCGATGAACCA (SEQ ID NO: 8) | 131 |
| Nestin | Fwd: GCCCTGACCACTCCAGTTTA (SEQ ID NO: 9)<br>Rev: GGAGTCCTGGATTTCCTTCC (SEQ ID NO: 10) | 200 |
| PDGFR-A | Fwd: TCTATGATCGTCCAGCCTCA (SEQ ID NO: 11)<br>Rev: TTCCTCGGGCAACTTGATAG (SEQ ID NO: 12) | 135 |
| PDGFR-B | Fwd: CATCGTGGTGCCACACTC (SEQ ID NO: 13)<br>Rev: GGATCTCGTAACGTGGCTTC (SEQ ID NO: 14) | 131 |
| Sox-2 | Fwd: GTATCAGGAGTTGTCAAGGCAGAG (SEQ ID NO: 15)<br>Rev: TCCTAGTCTTAAAGAGGCAGCAAAC (SEQ ID NO: 16) | 78 |
| TGFB-2 | Fwd: TTGACGTCTCAGCAATGGAG (SEQ ID NO: 17)<br>Rev: TCGCCTTCTGCTCTTGTTTT (SEQ ID NO: 18) | 196 |
| TGFBR-1 | Fwd: GCAAAGGTCGATTTGGAGAA (SEQ ID NO: 19)<br>Rev: CTGACACCAACCAGAGCTGA (SEQ ID NO: 20) | 207 |
| VEGF-A | Fwd: CCCTGATGAGATCGAGTACATCTT (SEQ ID NO: 21)<br>Rev: ACCGCCTCGGCTTGTCAC (SEQ ID NO: 22) | 248 |
| VEGFR-2 | Fwd: CAGCATCACCAGTAGCCAGA (SEQ ID NO: 23)<br>Rev: GTGGATACACTTTCGCGATG (SEQ ID NO: 24) | 187 |
| 18S | Fwd: TTCTTGGACCGGCGCAAG (SEQ ID NO: 25)<br>Rev: GCCGCATCGCCGGTCGG (SEQ ID NO: 26) | 142 |

| mRNA targets | Pre-designed primer sets (Invitrogen-ID) | product size (bp) |
| --- | --- | --- |
| Musashi 1 | HLUX 3007416 | 50-100 |
| CD133 | HLUX3014422 | 50-100 |
| uPAR | HLUX3008919 | 50-100 |
| hGAPDH | HLUX 100H-01 | 50-100 |

PERIPHERAL ZONE TUMOR CELLS, METHODS FOR THEIR PREPARATION AND USE

CROSS-REFERENCE TO RELATED APPLICATIONS

This application is the U.S. National Stage of International Application No. PCT/EP2009/006547, filed Sep. 9, 2009, which claims benefit of U.S. Provisional Patent Application No. 61/191,640, filed Sep. 10, 2008.

The present invention relates to a tumor cell of the peripheral zone of a tumor and methods of providing such a tumor cell. Further provided is a method for identifying a molecular marker diagnostic for an infiltrative cancer, an antibody, which specifically binds to such molecular marker, a method for identifying a therapeutic compound effective against a metastatic/infiltrative cancer disease and the use of a tumor cell according to the invention.

BACKGROUND OF THE INVENTION

Cancer is a disorder in which a population of cells has become, to varying degrees, unresponsive to the control mechanisms that normally govern proliferation and differentiation.

Cancer therapy can involve the modulation of enzymatic activity of target proteins in cancer cells. For example, as cancer cells are rapidly dividing they heavily rely on a sufficient supply of nucleotides to afford such rapid divisions. Thus, compounds were found which may be used to treat cancer and which inhibit enzymes used in purine and pyrimidine synthesis such as thymidylate synthase (TS), dihydrofolate reductase (DHFR), and glycinamide ribonucleotide formyl transferase (GARFT).

Despite the discovery of new anti-cancer drugs, the major driving force of mortality in human cancer diseases is in most cases still the recurrence of tumor growth after removal of the tumor by surgery and/or after standard chemotherapy/radiation therapy. A standard chemotherapy may comprise treating a patient and/or the tumor of the patient with alkylating agents, e.g. cisplatin and carboplatin, with anti-metabolites such as azathioprine or mercaptopurine, with plant alkaloids or terpenoids such as vinca alkaloids or taxanes, with podophyllotoxin, with topoisomerase inhibitors such as camptothecins, amsacrine, etoposide, with antitumour antibiotics such as dactinomycin, or also with monoclonal antibodies such as trastuzumab (Herceptin), cetuximab, and rituximab (Rituxan or Mabthera).

Therefore, there is a need for additional pharmaceutically active substances which can be used to treat cancer and which will effectively prevent recurrence of tumor growth after radiotherapy, chemotherapy and/or after tumor resection.

SUMMARY OF THE INVENTION

The inventors have identified a method which can be used to identify and preferably isolate a specific tumor cell in a population of different tumor cells, which is useful as a research tool for, e.g. defining new anti-cancer compounds that are effective to prevent the recurrence of cancer after radiotherapy, chemotherapy and/or after tumor resection. Thus, in a first aspect, the invention provides a method for providing a tumor cell comprising the steps:

(a) providing one cell or several cells of a first biopsy of a tumor centre;
(b) providing cells of a second biopsy of peripheral zone tissue surrounding the tumor centre in step (a); and
(c) selecting at least one tumor cell from the cells provided in step (b), wherein the selected tumor cell has at least one of the following features:
  (i) the selected tumor cell expresses the protein and/or the mRNA of the cellular marker CD133 in a concentration which is lower than the concentration or the average concentration of this marker in the one cell or in the several cells provided in step (a), respectively;
  (ii) the selected tumor cell expresses the protein and/or the mRNA of the cellular marker CD87 in a concentration which is higher than the concentration or the average concentration of this marker in the one cell or in the several cells provided in step (a), respectively;
  (iii) the selected tumor cell expresses the protein and/or the mRNA of the cellular marker VEGFR-2 in a concentration which is lower than the concentration or the average concentration of this marker in the one cell or in the several cells provided in step (a), respectively;
  (iv) the selected tumor cell expresses the protein and/or the mRNA of the cellular marker PDGFR-B in a concentration which is higher than the concentration or the average concentration of this marker in the one cell or in the several cells provided in step (a), respectively;
  (v) the cell division rate of the selected tumor cell is greater than the cell division rate or the average cell division rate of the one cell or of the several cells provided in step (a), respectively; and/or
  (vi) the cell motility of the selected tumor cell is greater than the cell motility or the average cell motility of the one cell or of the several cells provided in step (a), respectively.

In a further aspect of above method step (a) is not carried out and the selection is based on the expression of markers (i), (ii), (iii) or (iv) or features (v) or (vi) or any combination thereof.

In a further aspect, the invention provides a method for providing a tumor cell comprising the steps:

(a) obtaining cells of a biopsy of peripheral zone tissue surrounding a tumor centre (a);
(b) passaging and/or growing said cells in tissue culture until at least 90% of the cells are tumor cells having at least one of the following features:
  (i) the tumor cell expresses the protein and/or the mRNA of the cellular marker CD133 in a concentration which is lower than the concentration or the average concentration of this marker in a cell or in several cells from a tumor centre of the same tumor type, preferably the same tumor;
  (ii) the selected tumor cell expresses the protein and/or the mRNA of the cellular marker CD87 in a concentration which is higher than the concentration or the average concentration of this marker in a cell or in several cells from a tumor centre of the same tumor type, preferably the same tumor;
  (iii) the selected tumor cell expresses the protein and/or the mRNA of the cellular marker VEGFR-2 in a concentration which is lower than the concentration or the average concentration of this marker in a cell or in several cells from a tumor centre of the same tumor type, preferably the same tumor;
  (iv) the selected tumor cell expresses the protein and/or the mRNA of the cellular marker PDGFR-B in a concentration which is higher than the concentration or the average concentration of this marker in a cell or in several cells from a tumor centre of the same tumor type, preferably the same tumor;

(v) the cell division rate of the selected tumor cell is greater than the cell division rate or the average cell division rate of the cell or of several cells of a tumor centre of the same tumor type, preferably the same tumor; and/or (vi) the cell motility of the selected tumor cell is greater than the cell motility or the average cell motility of the cell or of several cells of a tumor centre of the same tumor type, preferably the same tumor.

In a further aspect the invention concerns a tumor cell obtainable by a method according to the invention.

The invention also provides in a further aspect a tumor cell expressing the protein and/or the mRNA of the cellular marker CD133, CD87, VEGFR-2 and/or PDGFR-B.

In addition, the invention provides a tumor cell composition, wherein at least 60%, preferably 70% and most preferably 80% of the cells comprised therein express the protein and/or the mRNA of the cellular markers CD87 and/or PDGFR-B.

The invention further provides a method for identifying a therapeutic compound effective against a metastatic cancer disease comprising the steps:
(a) contacting a tumor cell or a tumor cell composition according to the invention with a test compound; and
(b) selecting a test compound as the therapeutic compound which is cytotoxic, cytostatic for said tumor cell or tumor cell composition and/or induces cell differentiation for said tumor cell or tumor cell composition.

The invention further provides a method for identifying a molecular marker diagnostic for an infiltrative cancer comprising the steps:
(a) providing at least one tumor cell according to the invention;
(b) providing at least one cell of the tumor centre, the peripheral zone of which said tumor cell of step (a) was obtained from; and
(c) selecting, as the molecular marker, a molecule which
  (i) is present in the at least one tumor cell provided in step (a) but not in the at least one cell provided in step (b); or
  (ii) is present in the at least one tumor cell provided in step (a) and in the at least one cell provided in step (b) but wherein the molecular marker in the at least one tumor cell provided in step (a) is present at a concentration which is at least 50% higher or at least 50% lower than the concentration of said marker in the at least one cell provided in step (b).

Further provided is an antibody, which specifically binds to the molecular marker obtainable, using the method according to the invention or to a tumor cell according to the invention.

A further aspect of the invention concerns the use of a tumor cell according to the invention and/or the molecular marker obtainable using the method according to the invention
(i) as a positive control sample for the diagnosis and/or prognosis of a cancer disease;
(ii) as a vaccine; and/or
(iii) for the preparation of a therapeutic dendritic cell vaccine.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages different aspects of the invention are defined in more detail. Each aspect so defined may be combined with any other aspect or aspects unless clearly indicated to the contrary. In particular, any feature indicated as being optional, preferred or advantageous may be combined with any other feature or features indicated as being optional, preferred or advantageous.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. Reference numbers appear in parenthesis and are listed at the end of the example section.

In the following, a short summary of relevant molecular markers is provided that are discussed in the context of the present invention. The clusters of differentiation (CD) nomenclature may be used to designate surface markers of cells. Thus, following this nomenclature standard, CD133 as used herein is the protein designated "prominin 1" or a mRNA encoding this protein or any homologue or orthologue of this protein. Prominin 1 is a glycoprotein that is expressed, for example, in hematopoietic stem cells, endothelial progenitor cells, glioblastomas, neuronal and glial stem cells and in other cell types. Also following CD nomenclature, CD87 is urokinase-type Plasminogen Activator Receptor (uPAR), which is a part of the plasminogen activation system, which in the healthy body is involved in tissue reorganization events such as mammary gland involution and wound healing. uPAR binds urokinase which is a serine protease involved in the activation of plasmin which in turn triggers a protease cascade which ultimately is able to degrade e.g. extracellular matrix. Cellular markers that have been assigned a CD number are very well known in the art and the respective protein and mRNA sequences are readily available for various species on various public databases. For example, human CD133 protein can have a polypeptide sequence according to SEQ ID NO: 1 and the respective mRNA can, for example, have the polynucleotide sequence according to SEQ ID NO: 2. Human CD87 protein has typically the polypeptide sequence SEQ ID NO: 3 and the respective mRNA a sequence according to SEQ ID NO: 4. Other relevant markers are the human platelet-derived growth factor receptor A (PDGFR-A) (Accession NO: NM_006206), the human platelet-derived growth factor receptor B (PDGFR-B) (Accession NO: NM_002609), the human transforming growth factor-beta 2 (TGFB-2) (Accession NO: NM_003238), the human transforming growth factor-beta receptor 1 (TGFBR-1) (Accession NO: NM_004612), the human vascular endothelial growth factor A (VEGF-A) (Accession NO: NM_003376), the human vascular endothelial growth factor receptor 2 (VEGFR-2) (Accession NO: NM_002253), the human CD44 (cluster of differentiation 44) (Accession NO: NM_000610) and the human L1 (also known as L1CAM, L1CAM has also been designated as CD171 (cluster of differentiation 171)) (Accession NO: NM_000425). It is to be understood that, depending on the origin of the tumor and the genetic variations typically found in tumor cells, the protein and/or mRNA sequences of cellular markers like CD133, CD87, PDGFR-A, PDGFR-B, TGFB-2, TGFBR-1, VEGF-A, VEGFR-2, CD44 and L1 may comprise mutations, deletions or insertions. Thus, the protein and mRNA sequences of the cellular markers may vary depending on the individual biopsy. Thus, also proteins that have over the entire length a sequence identity of more than 80%, 85%, 90% or more than 95% with a molecular marker used in the invention, e.g. CD133 according to SEQ ID NO: 1, and CD87 according to SEQ ID NO: 3, are considered to fall within the meaning of the respective marker. Similarly, when quantifying the abundance of a RNA polynucleotide that encodes a marker used in the invention, also polynucleotides can be quantified that are at least 85%, 90%, 95%, 96%, 97%, 98%, or at least 99% identical with a polynucleotide encoding a marker used in the invention, e.g. such as SEQ ID NO: 2 and 4. When determining the percent identity of a polynucleotide it is preferred to determine the percent identity over the entire length of the coding region of the polynucleotide used in the invention. Sufficient antibodies for all cellular markers used herein are available in the art to readily detect also mutant protein forms of these markers, e.g. variant forms of CD133 and CD87. Also the marker-specific oligonucleotide primers that can be used for example in real-time PCR to quantify mRNA encoding these marker proteins (see also below) can be readily designed by the average skilled person without undue burden, taking into consideration any potentially present sequence mutation, deletion and insertion.

Glial fibrillary acidic protein (GFAP) is an intermediate filament (IF) protein, e.g. as expressed in astrocytes and can be detected by anti-GFAP antibodies available in the state of the art. The presence of B-III tubulin, e.g. as present in a neuron can be detected by anti-B-III tubulin antibodies. The molecular marker CNPase is a 2',3'-cyclic-nucleotide 3'-phosphodiesterase and expressed e.g. in oligodendrocytes. The Ki-67 protein (also known as antigen identified by monoclonal antibody Ki-67 or MKI67) is a cellular marker for proliferation. It can also be detected using a monoclonal antibody designated as MIB-1.

One of the hallmark features of human malignant cancer is the infiltrative nature of individual tumor cells (see e.g. ref. 1) that migrate away from a hypothetical point of origin, populating the surrounding native tissue. Even if a surgeon succeeds in complete macroscopic resection of the tumor, always, at least a few malignant cells stay behind (FIG. 1A). In the past, these 'remaining' cells have been made responsible for the recurrence of disease (2, 3). Recurrence of disease occurs months after standard therapy in these patients. For example, patients suffering from human glioblastoma (GBM) show a median overall survival of 14.6 months, despite combined and optimized surgical, radio-, and chemotherapeutic measures (4). It has been assumed for years that malignant cells in the tumor centre and in the infiltrated periphery have common characteristics, and thus, tissue available from standard surgical resection served for all necessary experimental analyses.

The present inventors succeeded in isolating cells found in the centre of tumor tissue and cells from the peripheral zone surrounding the tumor centre (the resection margin exposed after routine neurosurgery). A comparison of these cells derived from different tissue locations resulted in the unexpected observation that these tumor cells differ depending on their location. Thus, cells from the tumor centre and the tumor infiltration zone vary in various properties such as, for example, division rate, motility and the abundance of molecular markers. Without being bound by theory, the difficulty of removing potentially remaining cells after tumor resection by using chemotherapy for example, could now be explained by the mentioned differences in tumor cell "behaviour" and the differences in molecular markers of these cells. Consequently, established chemotherapeutic treatments which have been developed using tumor cells of the tumor centre and which are, thus, effective primarily against tumor cells of the tumor centre, are expected to be less efficient or ineffective against tumor cells which reside in the tumor periphery and which are more likely to remain in the patient after resection of the tumor core, i.e. the tumor centre. Therefore, the provision of a method to identify and/or isolate such peripheral zone tumor cells, which are preferably additionally resistant against a standard chemotherapy, opens the possibility of e.g. searching for improved medications or chemotherapeutics that can be administered e.g. post-surgery to ameliorate the survival rate of the patients and to prevent or suppress the recurrence of secondary tumors.

Thus, in a first aspect, the invention provides a method for providing a tumor cell comprising the steps:
(a) providing one cell or several cells of a first biopsy of a tumor centre;
(b) providing cells of a second biopsy of peripheral zone tissue surrounding the tumor centre in step (a); and
(c) selecting at least one tumor cell from the cells provided in step (b), wherein the selected tumor cell has at least one of the following features:
　(i) the selected tumor cell expresses the protein and/or the mRNA, preferably the mRNA, of the cellular marker CD133 in a concentration which is lower than the concentration or the average concentration of this marker in the one cell or in the several cells provided in step (a), respectively;
　(ii) the selected tumor cell expresses the protein and/or the mRNA, preferably the mRNA, of the cellular marker CD87 in a concentration which is higher than the concentration or the average concentration of this marker in the one cell or in the several cells provided in step (a), respectively;
　(iii) the selected tumor cell expresses the protein and/or the mRNA of the cellular marker VEGFR-2 in a concentration which is lower than the concentration or the average concentration of this marker in the one cell or in the several cells provided in step (a), respectively;
　(iv) the selected tumor cell expresses the protein and/or the mRNA of the cellular marker PDGFR-B in a concentration which is higher than the concentration or the average concentration of this marker in the one cell or in the several cells provided in step (a), respectively;
　(v) the cell division rate of the selected tumor cell is greater than the cell division rate or the average cell division rate of the one cell or of the several cells provided in step (a), respectively; and/or
　(vi) the cell motility of the selected tumor cell is greater than the cell motility or the average cell motility of the one cell or of the several cells provided in step (a), respectively.

It is preferred that the comparative analysis of the cells of the tumor center and the cells of the peripheral zone tissue surrounding the tumor centre are conducted after passaging the cells from the peripheral zone tissue (step b) and/or from the tumor centre (step a), preferably after 5 to 10 cell culture passages.

Preferably, the at least one selected tumor cell from the tumor periphery expresses the cellular markers CD87 and/or PDGFR-B in a concentration which is at about 5%, 10%, 15%, 20% or 25%, more preferably at about 30%, 35%, 40%, 45%, 50%, 55%, or 60% and most preferably at about 65%, 70%, 75% or 80% higher or more than 80% higher than the concentration or the average concentration of these markers in the one cell or in the several cells provided in step (a).

It is also preferred that the selected tumor cell expresses the cellular markers CD133 and/or VEGFR-2 in a concentration which is at about 5%, 10%, 15%, 20% or 25%, more preferably at about 30%, 35%, 40%, 45%, 50%, 55%, or 60% and most preferably at about 65%, 70%, 75%, or 80% lower or more than 80% lower than the concentration or the average concentration of these markers in the one cell or in the several cells provided in step (a). It is particularly preferred that the cellular markers CD133 and/or VEGFR-2 are not expressed in at least one the selected tumor cell.

As the first biopsy is of a tumor centre and the second biopsy is of peripheral zone tissue, surrounding the tumor centre, it is preferred that the tissue locations for the two biopsies are mutually exclusive, e.g. the peripheral zone comprises a significantly different population of tumor cells compared to those typically found in the tumor centre.

As used herein, a "tumor" is one or more cells which exhibit an abnormal proliferation, usually caused by one or more genetic mutations present in said cells. Surgeons typically define tissue of the "tumor centre" in comparison to a tissue of the surrounding peripheral zone tissue in that it (i) exhibits a different consistency, e.g. an increased cell density, (ii) exhibits less structure, e.g. having a uniform visual appearance at low magnification (e.g. at 2× magnification) and/or (iii) exhibits an abnormal vascularisation, e.g. an increase in vascularisation. Furthermore, the tumor centre may show abnormal grouping of cells and occasional mitotic figures. Surgeons typically cannot access the histological features that define tumor cells, e.g. abnormal grouping of cells, or a mitotic figure that refers to a cell which is currently dividing, i.e. which is not in interphase, during an operation procedure. Those features, including cells, which are not in interphase exhibiting chromosomal condensations can, however, be routinely visualized during histological evaluation of surgery-derived tissue, such as of a biopsy, using for example a Hematoxylin and Eosin (H&E) staining protocol well known in the art of histology. Thus, in a further preferred embodiment, a biopsy tissue can be selected which fulfils some or all of the above criteria of a tumor centre. FIG. 9 indicates that surgeons are well capable of discerning between tumor centre and tumor periphery on the basis of above criterions. FIG. 9 shows the postoperative histological assessment of biopsies from tissue, which was considered by the surgeon on the basis of above criteria to be tumor centre and tumor periphery, respectively. With the exception of one case (see patient 017) out of 30 in all cases the tissue perceived to be from the tumor centre on the basis of later histological analysis in fact comprised entirely or primarily glioblastoma multiforme tissue. In the one exception the biopsy comprised glioblastoma multiforme tissue and tissue of the tumor periphery. The determination of tissue to be part of the tumor periphery by the surgeon proved to be similarly accurate. Out of 30 biopsies taken from tissue perceived on the bais of above criteria to be tumor periphery only one on the basis of the histological analysis later proved to be glioblastoma multiforme tissue (see patient 015). The rest of the biopsies was histologically proven to comprise at least primarily or entirely tissue of the tumor periphery.

Thus, the tumor centre refers to tissue, which is easily recognized by a surgeon examining the operation site in situ, and which will be resected in a first surgical procedure with the aim to cure the patient of cancer. Additional preferred meanings of "tumor centre" are provided in the preferred embodiments stated herein. With respect to this invention, "tumor" refers to any tumor, i.e. it may be derived from any organ or tissue. However, as also mentioned in more detail below, in a preferred embodiment of the method of the invention, the tumor is a brain tumor, more preferably a glioma and most preferably a Glioblastoma Multiforme. In one embodiment, the tumor may be a metastasizing or an infiltrating tumor.

The term "biopsy" refers to a cell, cells and/or tissue removed from a human or animal body, preferably as a sample. A biopsy comprises at least one, two, three, four, five, six, seven, eight, nine, ten, twenty, fifty, hundred or at least one thousand cells or more, e.g. 2000, 3000, 4000, 5000, 6000, 7000, 8000, 9000, 10 000, 12 000, 14 000, 16 000, 18 000, or 20 000 cells. Most preferably a biopsy comprises at least one or at least two cells. Preferably, the first and the second biopsy each comprise at least one or at least two tumor cells. In this respect it is noted that, preferably, the method of the invention is carried out in vitro, i.e. the method uses the material of a first and a second biopsy which is obtainable from a physician/surgeon or an external provider. The cells comprised in the biopsy are usually individualized for analysis or growth prior to analysis or further use as is well known in the art. Such individualization of cells without destroying the cells is commonly achieved by protease treatment, e.g. trypzination of the cell or tissue sample. Preferably such individualized cells are passaged for one or more times. Thus, the method of the invention can be carried out in vitro. "Selecting" in step (c) has in a preferred embodiment of the method, the meaning of "isolating".

As used herein, the term "surrounding" is to be understood as the common meaning of this verb. In general, "surrounding" refers to a limited spatial distance between the surrounding tissue and the tumor centre tissue. A biopsy sample of a peripheral zone tissue must comprise at least one tumor cell. Thus, in general, the peripheral zone tissue is the tissue that (i) embeds but does not comprise the tumor centre tissue and/or which (ii) comprises all infiltrating tumor cells which are tumor cells not located in the tumor centre tissue but which have spread from the tumor centre into the tissue surrounding the tumor centre. Thus, the peripheral zone reaches from the surface of the centre tumor tissue outwards into the non-centre tumor tissue. The outer delimitation of the peripheral zone is determined by the most remotely localized infiltrating tumor cell. If the tumor does not release any infiltrating tumor cells into its surrounding tissue, it is preferred that the peripheral zone defines a surface layer of the tumor and the tumor center (tumor core) is the tissue which lies beneath and contacts the peripheral zone tissue. Preferably, the peripheral zone envelopes the entire tumor center tissue.

The thickness of the peripheral zone will depend on the tumor size and/or the invasiveness of the tumor, i.e. the larger the tumor and the more invasive the tumor the thicker the peripheral zone surrounding the tumor. It is clear that depending on the shape of the tumor centre the thickness of the peripheral zone will vary around the circumference of the tumor centre. Thus, the "average thickness" of a peripheral zone characterizes the thickness of the peripheral zone as measured from the surface of the tumor centre to the most remotely localized infiltrating tumor cell detectable at least two instances. Typically the peripheral zone around the tumor centre has an average thickness of between 1 mm and 60 mm, more commonly between 5 mm and 50 mm and most commonly between 10 mm and 30 mm. To provide cells from this area it is desired to provide cells from a biopsy sufficiently remote from the tumor centre to exclude contamination with tumor cells from the tumor centre.

Thus, when providing cells of the surrounding peripheral zone tissue in step (b), the tissue is preferably selected from a tissue zone of between 0.5 mm to 60 mm surrounding the tumor centre, more preferably from a zone of between 1.0 to 40 mm and most preferably 2.0 to 30 mm. It is further preferred that the biopsy comprises cells which are located not further than about 60 mm, 50 mm, 40 mm, 30 mm, 20 mm, 10 mm, 9 mm, 8 mm, 7 mm, 6 mm, 5 mm, 4 mm, 3 mm or 2 mm away from the surface of the tumor centre. It is further preferred that alternatively, or additionally, the peripheral zone does not comprise any cells that are located less than 20 mm, 18 mm, 16 mm, 14 mm, 12 mm, 10 mm, 9 mm, 8 mm, 7 mm, 6 mm, 5 mm, 4 mm, 3 mm, or less than 2 mm, most preferably less than 2 mm away from the surface of the tumor centre.

In addition or alternatively to fulfilling above distance requirement the samples of the peripheral zone in step (b) are provided from a peripheral zone tissue that is characterized by an average tumor cell density, i.e. the presence of tumor cells which are selectable according to the method of the invention, of between 1 and 30 tumor cells per 100 healthy, non-tumor cells. More preferably, the samples are provided from peripheral zone tissue that is characterized by a tumor cell density, of between 1 and 20, between 1 and 15 and between 1 and 10, most preferably between 1 and 15, tumor cells per 100 healthy, non-tumor cells.

It is further preferred that in step (c) of the method of the invention, a tumor cell is selected that fulfils at least criterion (ii) and/or (iv). More preferably a tumor cell is selected that fulfils at least criteria (i) and (ii), at least criteria (i) and (iii), at least criteria (i) and (iv), at least criteria (i) and (v), at least criteria (i) and (vi), at least criteria (ii) and (iii), at least criteria (ii) and (iv), at least criteria (ii) and (v), at least criteria (ii) and (vi), at least criteria (iii) and (iv), at least criteria (iii) and (v), at least criteria (iii) and (vi), at least criteria (iv) and (v), at least criteria (iv) and (vi), or at least criteria (v) and (vi). In a further embodiment of the method, a tumor cell is selected that fulfils at least criteria (i), (ii), and (iii), at least criteria (i), (ii), and (iv), at least criteria (i), (ii) and (v), at least criteria (i), (ii) and (vi), at least criteria (ii), (iii) and (iv), at least criteria (ii), (iii) and (v), at least criteria (ii), (iii) and (vi), at least criteria (ii), (iv) and (v), at least criteria (ii), (iv) and (vi), at least criteria (ii), (v) and (vi), at least criteria (iii), (iv) and (v), at least criteria (iii), (iv) and (vi), at least criteria (iii), (v) and (vi), at least criteria (i), (ii), (iii) and (iv), at least criteria (i), (ii), (iii) and (v), at least criteria (i), (ii), (iii) and (vi), at least criteria (i), (iii), (iv) and (v), at least criteria (i), (iii), (iv) and (vi), at least criteria (i), (iii), (v) and (vi), at least criteria (i), (ii), (iv), and (v), at least criteria (i), (ii), (iv), and (vi), at least criteria (i), (ii), (v), and (vi), at least criteria (i), (ii), (iii), (iv) and (v), at least criteria (i), (ii), (iii), (iv) and (vi) and at least criteria (i), (ii), (iii), (iv), (v) and (vi).

If in step (a) one cell is provided for the purpose of comparing it with one cell provided in step (b), it is preferred that that cell is a tumor cell. Consistently, in this case it is also preferred that the one cell provide in step (b) is also a tumor cell. To provide a single tumor cell in step (a) and/or (b) it may be required to subselect such tumor cells from the tumor centre biopsy and peripheral zone tissue, respectively. If more than one cell is provided in step (a) and/or (b) an average of the characteristics (i) to (vi) may be determined. This average will also average the characteristics (i) to (vi) including non-tumor cells, if no selection for tumor cells is carried out when providing the cells in step (a) and/or (b). Thus, to provide comparability between, in particular characteristics (i) and (ii), (iii) and (iv), (i) and (iv) or (ii) and (iii), it is preferable that the same number of non-tumor cells are comprised in the cell sample provided in (a) and/or (b). A "tumor cell" as used throughout the specification is a cell comprising a genetic abnormality which preferably causes (i) an over-expression of at least one oncogene selected from the group consisting of: c-S is, epidermal growth factor receptor (EGFR), platelet-derived growth factor receptor (PDGFR), e.g. PDGFR-A or PDGFR-B, vascular endothelial growth factor receptor (VEGFR), HER2/neu, a tyrosine kinase such as a member of the Src-family, a member of the Syk-ZAP-70 family or a member of the BTK family; Abl; a Raf kinase; a cyclin-dependent kinase; a GTPases such as Ras and a transcription factor such as myc and/or (ii) a reduction of the transcription and/or translation of a tumor-suppressor gene selected from the group consisting of: Retinoblastoma protein, p53, PTEN, APC, CD95 and a DNA repair protein.

Tumor cells may also or alternatively be characterized directly by their genetic abnormality, i.e. gene amplification (e.g. as in the case of CDK4 or MDM2), rearrangements (e.g. as in c-abl), chromosomal duplications, e.g. triploidy, tetraploidy, etc. (as for chromosme 10 in glioblastoma multiforme). A large number of such different abnormalities have been described for various tumors and tumor-subgroups (regularly updated on http://cancergenome.nih.gov/index.asp; for recent data on Glioblastoma see: The Cancer Genome Atlas Research Network. Comprehensive genomic characterization defines human glioblastoma genes and core pathways. Nature. 2008; 455:1061-1068.).

In order to be able to select a tumor cell in step (c), one or several of the features as outlined under (i) through (vi) must be known or determined for the one or several cells provided in step (a) and (b). If only one cell is provided in step (a), the features (i) through (vi) can each independently be determined for this single cell. If multiple features selected from (i) through (vi) need to be determined, the features can also be determined for this single cell. For example, the cell motility is measured first, e.g. using time-lapse video-microscopy. Next, the cell can be contacted with fluorescence-labeled marker specific antibodies and the fluorescence signal can be quantified using e.g. fluorescence microscopy. Finally, the cell division rate can be determined in culture. Although all features (i) through (vi) can be determined for a single living cell as outlined above, it is preferred that when multiple features are to be determined for one cell of (a) and/or (b), then the cell is multiplied using clonal expansion using cell culturing methodology, before determining features (i) through (vi). Thus, to determine the features of a cell provided in (a) or (b), these cells may conveniently be first expanded and then dispensed into e.g. a multi-well plate. All experiments necessary to quantify the features (i) through (vi) can then preferably be carried out directly in the multi-well plate. Using this approach, a large number of cells can be screened without undue burden.

It is noted that when the features of a cell in (a) must be determined, it is not important that the cell remains alive for later use. Thus, to determine only features (i) and/or (ii), (iii) and/or (iv), (i) and/or (iv), or (ii) and/or (iii) of a cell in (a), this can be done also by fixing the cell using e.g. paraformaldehyde and by following immunohistochemical protocols available in the art to stain and quantify the cells for the respective markers CD133 and/or CD87, VEGFR-2 and/or PDGFR-B, CD133 and/or PDGFR-B, or CD87 and/or VEGFR-2, respectively. If additionally also features (v) and (vi) are to be determined for a single cell, these experiments will have to be carried out before fixing, i.e. before determining the features (i) and/or (ii), (iii) and/or (iv), (i) and/or (iv), or (ii) and/or (iii).

In all cases FACS analysis may be applied to determine cell division, and/or to quantify one or more of the cellular markers such as in features (i) and (ii) or (iii) and (iv). FACS analysis has the advantage that a cell can be recollected alive after it has been assayed.

If only one cell is provided in step (a) then the quantified values for features (i), (ii), (iii), (iv), (v) and/or (vi) of that one cell can be compared with the respective features of a cell provided in step (b). If more than one cell is provided in step (a) then it is preferred to use the average of quantified values known or determined for each feature, when selecting the tumor cell in step (c).

In another embodiment of the method of the invention, the first (tumor centre) and the second (tumor periphery) biopsy are obtained during the same surgical procedure. In a further embodiment of the method of the invention, the second biopsy is obtained at a later time point, in a second surgical procedure after the tumor centre had been removed in an earlier first surgical procedure. In the latter case, the peripheral zone comprises tissue, which directly contacts the "hole" in the tissue where the tumor centre used to be (representing the resection margin of routine neurosurgical procedure).

It is further preferred that in step (a) and/or in step (b) at least one cell is expanded in vitro using cell culture methodology prior to step (c). Thus, cells of the first and/or the second tissue biopsy may be cultivated, e.g. as described in the examples herein, to e.g. obtain individual cells from the biopsy. The cells are preferably held in culture for at least 10, 20, 30 or at least 60 minutes or for at least 1, 2, 3, 4, 5, 6, or for at least 7 days before carrying out step (c). More preferably the cells obtained in step (a) and/or step (b) are passaged at least one time, preferably at least 2, 3, 4, 5, 6, 7, 8, 9, or 10 times most preferably at least 5 times after the cells of the biopsy have been placed in cell culture. The term "passaging of cells" is well understood in the art of cell culture. It refers to the growth of cells in an appropriate medium comprising nutrients required for growth of the cells. Such growth can be, e.g. on tissue culture plates or in suspension culture. Once the cells reach a certain density and/or before they become contact inhibited, they are harvested and transferred to a new cell culture container (e.g. culture plate or roller bottle) at a lower density per milliliter culture medium as harvested. The number of cells not capable of proliferating under the culture conditions or which have a lower capacity of proliferation than other cells comprised in the biopsy, will decrease by each dilution step. Eventually, the cell population will primarily comprise or consist of cells having a similar proliferative capacity under the respective conditions. It can be taken from FIG. 10 that after five passages cells from either the tumor centre or cells from the tumor periphery essentially comprised only tumor cells on the basis of the presence of amplifications of CDK4 and MDM2 genes. Accordingly, in other aspects of the present invention as set out below, the tumor cells of the periphery are merely selected by obtaining a biopsy from the tumor periphery and culturing the cells under the cell population comprises primarily, e.g. more than 90%, preferably more than 95% or even 100% tumor cells. In this aspect the assessment of characteristics (i) to (v) are not used for selection of the cells but may be used at a later point to verify that the cells obtained at the end of the culturing step are indeed primarily tumor cells of the periphery. Similarly the tumor cell markers indicated above including chromosomal alterations can be used for such an assessment.

In general it is possible to determine the features of the cells used in the method of the invention at any point of time during the culturing of the cells. Furthermore, when determining multiple features, it is not necessary to determine all features at one point in time, i.e. in parallel. However, it is preferred that the features which are compared directly with each other are determined at comparable time points. Thus, for example, feature (iv) may be determined for a cell in (a) and (b) at one given point in time and feature (iii) may be determined for a cell in (a) and (b) at the same or a different point in time. Methods for primary cell culture and the isolation of single/individual cells using enzymes such as e.g. collagenase, trypsin, or pronase, which break down the extracellular matrix are well known in the art. Also cells of a nervous tissue sample can be held in cell culture (see e.g. Culturing nerve cells, $2^{nd}$ edition, edited by Gary Banker and Kimberly Goslin, The MIT Press, Cambridge, Mass., London, England, 1998).

In a further preferred embodiment of the method of the invention, the tumor centre of step (a) is defined in that it comprises a larger number of stem cells per unit volume of tissue than are comprised in the second biopsy of the peripheral zone tissue of step (b). Preferably the tumor centre comprises at least a 5%, 10%, 15%, 20%, 25%, 30%, 35%, 40%, 45%, 50%, 60%, 70%, 80%, 90%, 100%, 150% or at least 200% greater number of stem cells per unit volume of tissue than are comprised in the second biopsy. Preferably, one unit volume of tissue comprises or consists of 10, 100, 1 000, or 10 000 cells. As used herein, a "stem cell" or "stem cells" refers to a cell, or cells, respectively, that can self-renew, proliferate and that is/are multipotent (i.e. can give rise and/or differentiate into more than two different cell types typically found in the organ system the stem cell was derived from).

Preferably, the stem cells that are considered for above differentiation between tumor centre and peripheral tissue express at least one cellular marker selected from the group consisting of Nestin, Stat3, Kit, Sox1, Sox2, Msi1, Notch1, Melk, Pax6, CD44, BMI1, CD133, GFAP, SSEA-1, and PDGFRα. Commercial antibodies are readily available to determine the presence of these stem cell markers using e.g. FACS analysis or Western blot. Additionally the average skilled person can quantify without undue burden the relative copy number of mRNA expressed in a tumor and/or stem cell using e.g. real-time quantitative PCR as e.g. outlined in the examples. Thus, the quantity of protein and/or mRNA of any of the markers used herein such as e.g. CD133 and CD87 can be easily determined using common laboratory equipment and assays routinely applied in the art.

It is further preferred that the stem cells, that are compared for the purpose of differentiating between the tumor centre and the peripheral zone, are multipotent stem cells that are capable of differentiating into astrocytes expressing GFAP, neurons expressing betaIII-tubulin and/or oligodendrocytes expressing CNPase.

In a further preferred embodiment of the method, the stem cell is capable of growing into a spherical cell aggregate when cultured in cell culture, preferably after a duration of at least 3, 4, 5, 6, 7, 8, 9, 10, 11, 12, 13, 14, 15, 20, 25, 28 or 30 days, most preferably after at least 7 days. Preferably, the tumor centre comprises at least a 5%, 10%, 15%, 20%, 25%, 30%, 35%, 40%, 45%, 50%, 60%, 70%, 80%, 90%, 100%, 150% or at least 200% greater number of stem cells per unit volume of tissue than are comprised in the second biopsy, wherein the stem cells are capable of forming spherical aggregates within 7 days in culture.

It is further preferred that the first biopsy is derived from a tumor centre which comprises an average tumor cell density of at least 50, 51, 52, 53, 54, 55, 56, 57, 58, 59 or at least 60 tumor cells, most preferably at least 50 tumor cells per 100 healthy, non-tumor cells.

In another embodiment of the method of the invention it is preferred that the first biopsy is derived from a tumor of a tissue selected from the group consisting of lip, oral cavity tissue, skin, blood and/or hematopoietic system, pharynx, digestive system, a gland, a tissue of the respiratory system, bone, articular cartilage, skin, connective tissue, a tissue of the urogenital area, of the nervous system and of the endocrine system.

In this context it is preferred that the tumor is a tumor of the nervous system and that this tumor is a WHO-grade I, II, III, or IV glioma of the brain. In another preferred embodiment, the tumor is a tumor of the nervous system that is either a low-grade (i.e. diffuse) or a high-grade (i.e. malignant) glioma of the brain.

It is further preferred that the first biopsy comprises a larger number of cells per unit volume of tissue that express at least one of the proteins and/or mRNAs selected from the group consisting of GFAP, Map2c and Ki-67, than the number of cells comprised in the biopsy of the peripheral zone tissue of step (b).

In a further aspect of above method step (a) is not carried out and the selection is based on the expression of markers (i), (ii), (iii) or (iv) or features (v) or (vi) or any combination thereof and/or the selection is based on the presence of the markers characteristic of tumor cells indicated above, e.g. amplification of CDK4 and/or MDM2.

In a further aspect, the invention provides a method for providing a tumor cell comprising the steps:
(a) obtaining cells of a biopsy of peripheral zone tissue surrounding a tumor centre (a), preferably individualizing the cells from the biopsy;
(b) passaging and/or growing said cells in tissue culture until at least 90% of the cells are tumor cells having at least one of the following features:
  (i) the tumor cell expresses the protein and/or the mRNA of the cellular marker CD133 in a concentration which is lower than the concentration or the average concentration of this marker in a cell or in several cells from a tumor centre of the same tumor type, preferably the same tumor;
  (ii) the selected tumor cell expresses the protein and/or the mRNA of the cellular marker CD87 in a concentration which is higher than the concentration or the average concentration of this marker in a cell or in several cells from a tumor centre of the same tumor type, preferably the same tumor;
  (iii) the selected tumor cell expresses the protein and/or the mRNA of the cellular marker VEGFR-2 in a concentration which is lower than the concentration or the average concentration of this marker in a cell or in several cells from a tumor centre of the same tumor type, preferably the same tumor;
  (iv) the selected tumor cell expresses the protein and/or the mRNA of the cellular marker PDGFR-B in a concentration which is higher than the concentration or the average concentration of this marker in a cell or in several cells from a tumor centre of the same tumor type, preferably the same tumor;
  (v) the cell division rate of the selected tumor cell is greater than the cell division rate or the average cell division rate of the cell or of several cells of a tumor centre of the same tumor type, preferably the same tumor;
  (vi) the cell motility of the selected tumor cell is greater than the cell motility or the average cell motility of the cell or of several cells of a tumor centre of the same tumor type, preferably the same tumor and/or
  (vii) presence of one or more of the characteristics of tumor cells indicated above, preferably chromosomal aberrations, e.g. amplification of MDM2 and/or CDK4.

Typically at least 2 passages of the cells in cell culture are required to reduce the number of none-tumor cells in the cell composition to the desired level of 10% or less, preferably to 9%, 8%, 7%, 6%, 5%, 4%, 3%, 2%, 1% or less. Preferably the cells are passged at least 5 times to reach this level of homogeneity with respect to one or more of above indicated markers.

In a further aspect, the invention provides a tumor cell obtainable by any of the methods according to the invention.

Further provided is a tumor cell, preferably an isolated tumor cell, expressing the protein and/or the mRNA of the cellular markers CD133, CD87, VEGFR-2 and/or PDGFR-B. Preferably, the tumor cell is a brain tumor cell, more preferably a tumor cell of a glioma and most preferably a tumor cell of a Glioblastoma multiforme.

Preferably, the tumor cell of the invention is derived from the peripheral zone surrounding a tumor centre and wherein the cell
(i) expresses the cellular marker CD133 in a concentration which is lower than the average concentration of this marker in said tumor centre;
(ii) expresses the cellular marker CD87 in a concentration which is higher than the average concentration of this marker in said tumor centre;
(iii) expresses the cellular marker VEGFR-2 in a concentration which is lower than the average concentration of this marker in said tumor centre; and/or
(iv) expresses the cellular marker PDGFR-B in a concentration which is higher than the average concentration of this marker in said tumor centre.

Preferably, the tumor cell expresses the cellular markers CD87 and/or PDGFR-B in a concentration which is at about 5%, 10%, 15%, 20% or 25%, more preferably at about 30%, 35%, 40%, 45%, 50%, 55%, or 60% and most preferably at about 65%, 70%, 75% or 80% higher or more than 80% higher than the average concentration of these markers in the tumor centre.

It is also preferred that the tumor cell expresses the cellular markers CD133 and/or VEGFR-2 in a concentration which is at about 5%, 10%, 15%, 20% or 25%, more preferably at about 30%, 35%, 40%, 45%, 50%, 55%, or 60% and most preferably at about 65%, 70%, 75% or 80% lower or more than 80% lower than the average concentration of these markers in the tumor centre. It is particularly preferred that the cellular markers CD133 and/or VEGFR-2 are not expressed in the tumor cell.

The average concentration of a marker in the tumor centre is determined by determining the average concentration of the marker in a number of cells located in the tumor centre. When determining a marker concentration in a suitable assay, the number of cells used in the assay must be large enough such that tumor cells are comprised in the cells. The concentration of the markers can be quantified using standard methods such as FACS or Western Blott, using antibodies that are specific for the respective marker. Alternatively, also the absolute or relative concentration of mRNA encoding the marker may be determined by lysing the cells, purifying the mRNA (e.g. by precipitation) and by carrying out real-time PCR using primers which hybridize under stringent conditions solely to the marker mRNA. If an undefined number of cells is used in the assay, a relative concentration of the marker can be determined by standardizing the PCR amplification signal of the marker specific mRNA with a PCR amplification signal of a mRNA enocoding an internal control protein such as a housekeeping enzyme, for example GAPDH. Methods to conduct and quantitative real time PCR and quantitative Western Blot and FACS analysis are provided in the literature (see for example: RT-PCR Protocols. Methods in Molecular Biology, Vol. 193. Joe O'Connell, ed. Totowa, N.J.: Humana Press, 2002, 378 pp. ISBN 0-89603-875-0.) AND (Ormerod, M. G. (ed.) (2000) Flow cytometry—A practical approach. 3rd edition. Oxford University Press, Oxford, UK. ISBN 0-19-963824-1). Example 1 provides teachings of how to apply FACS-Analysis and qRT-PCR analysis to determine the presence of cellular markers.

It is preferred that the tumor cell according to the invention is a glioma cell of the brain. It is further preferred that the tumor centre is characterized by the presence of stem cells.

In a preferred embodiment, the tumor centre is derived from a cancer or tumor or is a cancer or tumor selected from the group consisting of:

fibrosarcoma, myxosarcoma, liposarcoma, chondrosarcoma, osteogenic sarcoma, chordoma, angiosarcoma, endotheliosarcoma, lymphangiosarcoma, mesothelioma, Ewing's tumor, lymphangioendotheliosarcoma, synovioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, astrocytic tumors (e.g., diffuse, infiltrating gliomas, anaplastic astrocytoma, glioblastoma, gliosarcoma, pilocytic astrocytoma, pleomorphic xanthoastrocytoma), oligodendroglial tumors and mixed gliomas (e.g., oligodendroglioma, anaplastic oligodendroglioma, oligoastrocytoma, anaplastic oligoastrocytoma), ependymal tumors (e.g., ependymoma, anaplastic ependymoma, myxopapillary ependymoma, subependymoma), choroid plexus tumors, neuroepithelial tumors of uncertain origin (astroblastoma, chordoid glioma, gliomatosis cerebri), neuronal and mixed-neuronal-glial tumors (e.g., ganglioglioma and gangliocytoma, desmoplastic infantile astrocytoma and ganglioglioma, dysembryoplastic neuroepithelial tumor, central neurocytoma, cerebellar liponeurocytoma, paraganglioglioma), pineal parenchymal tumors, embryonal tumors (medulloepithelioma, ependymoblastoma, medulloblastoma, primitive neuroectodermal tumor, atypical teratoid/rhabdoid tumor), peripheral neuroblastic tumors, tumors of cranial and peripheral nerves (e.g., schwannoma, neurinofibroma, perineurioma, malignant peripheral nerve sheath tumor), meningeal tumors (e.g., meningeomas, mesenchymal, non-meningothelial tumors, haemangiopericytomas, melanocytic lesions), germ cell tumors, tumors of the sellar region (e.g., craniopharyngioma, granular cell tumor of the neurohypophysis), hemangioblastoma, melanoma, and retinoblastoma.

The present invention further provides a tumor cell composition, wherein at least 60%, preferably 70% and most preferably 80%, 85%, 90%, 95%, 98%, 99%, 99.9%, or even 100% of the cells comprised therein express the protein and/or the mRNA of the cellular markers CD87 and/or PDGFR-B.

Most preferably, the tumor cell composition, wherein 100% of the cells comprised therein express the protein and/or the mRNA of the cellular markers CD87 and/or PDGFR-B, is a tumor cell composition derived from cell culture passages 5 to 10, i.e. cell culture passages 5, 6, 7, 8, 9 or 10.

Preferably, the cells comprised in the tumor cell composition are derived from the peripheral zone surrounding a tumor centre. It is also preferred that the cells which are comprised in the tumor cell composition and which express the cellular markers CD87 and/or PDGFR-B
 (i) express the cellular marker CD87 in a concentration which is higher than the average concentration of this marker in said tumor centre; and/or
 (ii) express the cellular marker PDGFR-B in a concentration which is higher than the average concentration of this marker in said tumor centre.

It is preferred that the cells comprised in the tumor cell composition which express the cellular markers CD87 and/or PDGFR-B, express said markers in a concentration which is at about 5%, 10%, 15%, 20% or 25%, more preferably at about 30%, 35%, 40%, 45%, 50%, 55%, or 60% and most preferably at about 65%, 70%, 75% or 80% higher or more than 80% higher than the average concentration of these markers in the tumor centre.

Preferably, the cells which are comprised in the tumor cell composition and which express the cellular markers CD87 and/or PDGFR-B further
 (iii) express the cellular marker CD133 in a concentration which is lower than the average concentration of this marker in said tumor centre; and/or
 (iv) express the cellular marker VEGFR-2 in a concentration which is lower than the average concentration of this marker in said tumor centre.

It is also preferred that the cells comprised in the tumor cell composition which express the cellular markers CD87 and/or PDGFR-B and which further express the cellular markers CD133 and/or VEGFR-2, express said markers in a concentration which is at about 5%, 10%, 15%, 20% or 25%, more preferably at about 30%, 35%, 40%, 45%, 50%, 55%, or 60% and most preferably at about 65%, 70%, 75% or 80% lower or more than 80% lower than the average concentration of these markers in the tumor centre.

In a preferred embodiment of the present invention, the cells which are comprised in the tumor cell composition express the cellular markers CD87 and/or PDGFR-B, but do not express the cellular markers CD133 and/or VEGFR-2. Thus, for example, the cells which are comprised in the tumor cell composition express CD87, but do not express PDGFR-B, CD133 and VEGFR-2. It is also possible that the cells which are comprised in the tumor cell composition express CD87 and PDGFR-B but do not express CD133 and VEGFR-2.

The average concentration of the cellular markers CD87 and/or PDGFR-B in the tumor centre is determined by determining the average concentration of said marker in a number of cells located in the tumor centre. The concentration of the cellular markers CD87 and/or PDGFR-B can be quantified using standard methods such as FACS or Western Blott, or using antibodies that are specific for the respective marker. The average concentration of the cellular markers CD87 and/ or PDGFR-B in the tumor centre is then compared with the concentration of the same cellular markers in the cells of the tumor cell composition derived from the peripheral zone surrounding the tumor centre which express the cellular markers CD87 and/or PDGFR-B, in order to determine, whether the concentration of said markers in said cells is higher or lower. For example, in case that 60 cells of 100 cells (i.e. 60%) of a tumor cell composition express the cellular marker CD87 and in case that the average concentration of the cellular marker CD87 in 100 cells of the tumor centre is "X" (i.e. arbitrary value), 60 cells of the 100 cells (i.e. 60%) of the tumor cell composition have to express said marker in a concentration which is higher than "X" in order to express the cellular marker in a higher concentration than the cells of the tumor centre.

Preferably, the tumor cell comprised in the tumor cell composition is a glioma cell of the brain and the tumor centre is characterized by the presence of stem cells.

In a preferred embodiment, the tumor centre is derived from a cancer or tumor or is a cancer or tumor selected from the group consisting of:

fibrosarcoma, myxosarcoma, liposarcoma, chondrosarcoma, osteogenic sarcoma, chordoma, angiosarcoma, endotheliosarcoma, lymphangiosarcoma, mesothelioma, Ewing's tumor, lymphangioendotheliosarcoma, synovioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, astrocytic tumors (e.g., diffuse, infiltrating gliomas, anaplastic astrocytoma, glioblastoma, gliosarcoma, pilocytic astrocytoma, pleomorphic xanthoastrocytoma), oligodendroglial tumors and mixed gliomas (e.g., oligodendroglioma, anaplastic oligodendroglioma, oligoastrocytoma, anaplastic oligoastrocytoma), ependymal tumors (e.g., ependymoma, anaplastic ependymoma, myxopapillary ependymoma, subependymoma), choroid plexus tumors, neuroepithelial tumors of uncertain origin (astroblastoma, chordoid glioma, gliomatosis cerebri), neuronal and mixed-neuronal-glial tumors (e.g., ganglioglioma and gangliocytoma, desmoplastic infantile astrocytoma and ganglioglioma, dysembryoplastic neuroepithelial tumor, central neurocytoma, cerebellar liponeurocytoma, paraganglioglioma), pineal parenchymal tumors, embryonal tumors (medulloepithelioma, ependymoblastoma, medulloblastoma, primitive neuroectodermal tumor, atypical teratoid/rhabdoid tumor), peripheral neuroblastic tumors, tumors of cranial and peripheral nerves (e.g., schwannoma, neurinofibroma, perineurioma, malignant peripheral nerve sheath tumor), meningeal tumors (e.g., meningeomas, mesenchymal, non-meningothelial tumors, haemangiopericytomas, melanocytic lesions), germ cell tumors, tumors of the sellar region (e.g., craniopharyngioma, granular cell tumor of the neurohypophysis), hemangioblastoma, melanoma, and retinoblastoma.

As mentioned above, the tumor cell of the invention is useful as it can be used to develop novel chemotherapeutics and/or diagnostics. Thus, further provided is a method for identifying a therapeutic compound effective against a metastatic cancer disease comprising the steps:

(a) contacting a tumor cell or a tumor cell composition according to the invention with a test compound; and
(b) selecting a test compound as the therapeutic compound which is cytotoxic, cytostatic for said tumor cell or tumor cell composition and/or induces cell differentiation of said tumor cell or tumor cell composition.

A cytotoxic compound will effectively kill the tumor cell or the tumor cells comprised in the tumor cell composition by inducing apoptosis and or necrosis. Viability and cytotixicity assays are widely available in the art. For example, alanyl-alanylphenylalanyl-aminoluciferin can be used to quantify cytotoxicity. This compound selectively detects dead cells when proteases from dead cells cleave this compound and induce a flash of light. Additionally and/or alternatively apoptosis markers can be measured to determine if a test compound induced apoptosis in a tumor cell or in a tumor cell composition of the invention. Such apoptosis markers comprise, e.g., caspase activity, preferably caspase-9 activity (see also U.S. Pat. No. 6,350,452 for novel apoptosis marker antibodies). Cytostatic compounds will stop the cell division, but will not necessarily result in cytotoxicity. Also the cytostatic effect that a test compound exerts onto a tumor cell or tumor cells composition of the invention can be determined using available assays such as by using dyes which label the DNA content of the cells. For example, the uptake of $^3$H-thymidine by tumor cells or by the tumor cell composition of the invention can be quantified. For the average skilled person in the art it will also be no burden to examine if a test compound induces differentiation of a tumor cell of the invention. A differentiation can be measured by examining the presence, absence or change of cell-type specific markers such as lipids and proteins that are specifically found only on a particular cell-type. Thus, the loss of expression of CD133 and/or CD87, for example, will indicate that a test compound effected a tumor cell differentiation.

With respect to the tumor cell composition, the percentage of cells affected by a test compound has to be determined. For this purpose, the number of cells in the tumor cell composition must be large enough such that tumor cells are comprised in the cells. The test compound is only regarded as a therapeutic compound having a cytotoxic, cytostatics effect for said tumor cell composition in the context of the present invention, whether at least 15% or 20%, preferably 30%, 40%, or 50% and most preferably 60% of the cells comprised in the tumor cell composition are affected by the test compound. In preferred embodiments, 75%, 80%, 85%, 90%, 95%, 98%, 99%, 99.9% or even 100% of the cells comprised in the tumor cell composition are affected by the test compound.

In addition, the test compound is only regarded as therapeutic compound inducing cell differentiation of said tumor cell composition in the context of the present invention, whether the cell differentiation is induced in at least 15% or 20%, preferably 30%, 40%, or 50% and most preferably 60% of the cells comprised in the tumor cell composition. In preferred embodiments, the test compound induced in 75%, 80%, 85%, 90%, 95%, 98%, 99%, 99.9% or even 100% of the cells comprised in the tumor cell composition cell differentiation.

For example, in case that 80 of 100 cells (i.e. 80%) of a tumor cell composition express the cellular marker CD87 and in case that 50 of said 100 cells are affected by the test compound (I.e. 50%), the test compound is reagarded as having a therapeutic effect.

In a preferred embodiment of the method of the invention, in step (b) a test compound is selected which has at least one of the following properties:
(i) it is more cytotoxic for said tumor cell than for a healthy, non-tumor cell;
(ii) it is more cytostatic for said tumor cell than for a healthy, non-tumor cell; and/or
(iii) it induces cell differentiation of said tumor cell.

In a further aspect the invention provides a method for identifying a molecular marker diagnostic for an infiltrative cancer comprising the steps:
(a) providing at least one tumor cell according to the invention;
(b) providing at least one cell of the tumor centre, preferably of a tumor centre the peripheral zone of which said tumor cell of step (a) was obtained from; and
(c) selecting, as the molecular marker, a molecule which
   (i) is present in the at least one tumor cell provided in step (a) but not in the at least one cell provided in step (b); or
   (ii) is present in the at least one tumor cell provided in step (a) and in the at least one cell provided in step (b) but wherein the molecular marker in the at least one tumor cell provided in step (a) is present at a concentration which is at least 10%, 20%, 30%, 40%, 50%, 60%, 70% and preferably at least 50% higher or at least 10%, 20%, 30%, 40%, 50%, 60%, 70% and preferably at least 50% lower than the concentration of said marker in the at least one cell provided in step (b).

An "infiltrative cancer" is a tumor tissue capable of disseminating tumor cells into a zone surrounding the tumor centre, e.g. a brain glioma.

Preferably, the molecular marker identified according to the method of the invention is a protein or a lipid. In a further preferred embodiment of the method of the invention, the molecular marker is present at a higher concentration in the at least one cell provided in step (a) than the at least one cell provided in step (b).

A further aspect of the invention is an antibody, which specifically binds to the molecular marker obtainable using the method according to the invention or to a tumor cell according to the invention. Antibodies can be generated either using established methods comprised in the art or by contracting with one of the many commercial customized antibody providers.

A tumor cell according to the invention and/or the molecular marker obtainable using the method according to the invention can be used as an internal reference standard in an assay which detects the presence of infiltrating tumor cells. For example the relative amounts of cell surface markers expressed in a tumor cell of the invention can be compared with the expression pattern of the same markers on a tissue or tissue sample from a subject. If there is a good correlation, e.g. better than 80% or better than 90%, the subject is considered at high risk of developing a tumor or the tissue of the subject already comprises infiltrated tumor cells. Alternatively or additionally, a tumor marker or tumor cell of the invention can also serve for the preparation of a vaccine useful in preventing and/or treating an infiltrating tumor or a cancer disease.

Thus, in another aspect, the invention provides the use of a tumor cell according to the invention and/or the molecular marker obtainable using the method according to the invention
(i) as a positive control sample for the diagnosis and/or prognosis of a cancer disease;
(ii) as a vaccine; and/or
(iii) for the preparation of a therapeutic dendritic cell vaccine.

If a tumor cell according to the invention and/or the molecular marker obtainable using the method according to the invention is used for vaccination, the cell and/or marker can be admixed with a pharmaceutically acceptable vaccine preparation. Particular preferred forms for the administration of a compound of the invention as vaccine are forms suitable for injectionable use and include sterile aqueous solutions or dispersions and sterile powders for the preparation of sterile injectable solutions or dispersion. Preparations for vaccination are known in the art. Preferably, the final solution or dispersion form must be sterile and fluid. Typically, such a solution or dispersion will include a solvent or dispersion medium, containing, for example, water-buffered aqueous solutions, e.g. biocompatible buffers, ethanol, polyol, such as glycerol, propylene glycol, polyethylene glycol, suitable mixtures thereof, surfactants or vegetable oils. Preferably, the vaccine preparation additionally comprises an adjuvant. The term "adjuvant" as used herein refers to substances, which when administered prior, together or after administration of an antigen/immunogen accelerates, prolong and/or enhances the quality and/or strength of an immune response to the antigen in comparison to the administration of the antigen alone, thus, reducing the quantity of antigen/immunogen necessary in any given vaccine, and/or the frequency of injection necessary in order to generate an adequate immune response to the antigen/immunogen of interest. Adjuvants include but are not limited to RIBI Detox™ QS21, alum and incomplete Freund's adjuvant. In one embodiment, the mutant ras peptide is administered in combination with Detox™ (RIBI Immunochem Research, Hamilton, Mont.). RIBI Detox™ contains as active ingredients the cell wall skeleton from *Mycobacterium phlei* and monophosphoryl lipid A from *Salmonella* minnesota R595 prepared as an oil-in-water emulsion with squalene and tween 80.

For vaccination, the preferably sterile tumor cell and/or molecular marker of the invention can be administered by various well known routes, including oral, rectal, intragastrical, intracranial and parenteral administration, e.g. intravenous, intramuscular, intranasal, intradermal, subcutaneous, and similar administration routes. Parenteral administration and particular intravenous administration, preferably by depot injection, is preferred.

It was shown that freeze-thawed or formaldehyde-fixed tumor antigens and heat-denatured tumor antigens elicited profound anti-tumor immune responses and greatly inhibited the growth of live tumor cells (Yoon T J, et. al., Exp Mol Med. 2008 Feb. 29; 40(1):130-44). Furthermore, therapeutic vaccines based on Dendritic Cells (DCs) carrying tumor antigens have emerged as a promising strategy to initiate an immune response against tumor cells. A tumor cell according to the invention comprises a multiplicity of tumor antigens such as the molecular marker obtainable using the method according to the invention. Thus, as mentioned, a tumor cell according to the invention and/or a molecular marker obtainable using the method according to the invention can also be used for the preparation of a therapeutic dendritic cell vaccine. Methods for preparation of such vaccine are provided e.g. in Yoon T J, et. al. supra. A DC vaccine can be prepared using various methodologies, such as by extraction of mRNA from the malignant cells and introduction of this mRNA into dendritic cells using electroporation and/or co-incubation. Alternatively, dendritic cells can also be loaded with tumor antigens selected from the group consisting of peptides of the tumor cell of the invention, whole protein isolated from said tumor cell, tumor cell lysate or apoptopic tumor cell debris. For detailed instructions of generating tumor-specific dendritic cells see: Juliana M Sousa-Canavez et. al., Genetic Vaccines and Therapy 2008, 6:2 and Gilboa E. et al (2007) J Clin. Invest.; 117(5):1195-203.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following figures and examples are merely illustrative of the present invention and should not be construed to limit the scope of the invention as indicated by the appended claims in any way.

BRIEF DESCRIPTION OF THE FIGURES

The file of this patent or application publication contains at least one drawing executed in color. Copies of this patent or application publication with color drawing(s) will be provided by the Office upon request and payment of the necessary fee.

FIG. 3: Immediate in vitro analysis. (A) Appearance of representative aggregates in non-adhesive culture conditions at 14±4 days in culture. Note that the centre biopsy samples, in general, yielded spherical structures while specimens from the tumor periphery appeared often less organized. (B) Results of viable cell counting indicate some considerable case-to-case variability, yet overall comparable numbers of cells in the periphery and the centre biopsy cultures at the end of the observation interval. The left column refers to the mean result of centre biopsy samples and the right column refers to the mean result of periphery biopsy samples. Scale bar in (A): 200 µm.

FIG. 5: Proliferation kinetics. (A) A representative example of cells at the initiation of analysis (passage 5). Note that this pair of cultures derived from the surgical procedure displayed in FIG. 1, and note moreover the morphological differences between centre and periphery cells. In general, a linear expansion was observed on a logarithmic scale without significant alteration of cell morphology under these conditions. The plot of growth kinetics of this particular pair of cultures is presented as inset. (B). Slope analysis of all samples investigated in this paradigm (patients 012, 013, 015, 016, 017, 020, 021, 023) revealed a significant difference between slower proliferating centre cultures and more rapidly expanding periphery biopsy-derived cells ($p=0.0039$). The insert shown in (A) is also shown again as an enlarged image on the bottom of this FIG. 5. The column pair in (B) consists of a left column referring to centre biopsy samples and a right column referring to periphery biopsy samples. Scale bar in (A), 20 µm.

FIG. 9: Patient data. Paired tissue samples were received from 30 GBM patients (18 males, 12 females). Patients were between 27 and 79 years old at the time of surgery, with the minority of cases representing relapsed disease. Applying the criteria outlined in FIG. 2, the histological features of each biopsy sample were verified using standard H&E staining, and immunohistochemistry applying antibodies against GFAP, MAP2c, and Ki67. Specifically, tissue showing vascular proliferation and necrosis, a presence of pleomorphic glial tumor cells, and an abundance of mitotic/proliferative activity was classified as GBM. Tissue exhibiting an increase in cellular density with abnormal grouping of pleomorphic glial cells and occasional mitotic figures was classified as glioma infiltration zone (INF). According to this histological classification, 24/30 (80%) of the GBM center biopsy samples showed exclusive morphological GBM signs. 24/30 (80%) periphery biopsy samples exhibited exclusive morphological signs of an INF, and in 11 of a total of 60 obtained biopsies (18%) mixed GBM and INF characteristics were detected. Exclusive INF features were never observed in center biopsy samples; however, exclusive GBM characteristics could be demonstrated in 1/30 (3%) periphery biopsy samples.

FIG. 11: Molecular marker analysis. Quantitative RT-PCR (qPCR) mean data demonstrating levels of the molecular targets VEGFR-2 (A), and PDGFR-B (B) from a set of six-paired culture samples of patients 013, 021, 023, 025, 035 and 046 (at culture passage 5). Note the regional distribution (topography) of VEGFR-2 (A), and PDGFR-B (B) (*p<0.05). VEGFR-2 (A), and PDGFR-B (B) are like CD133 and uPAR expressed in complementary patterns in periphery and centre cultures. For presentation in (A) and (B), original data were multiplied with a factor of $10^6$ as indicated on the y-axis.

FIG. 13: Primers. List of primers used for quantitative RT-PCR studies. Note that for Musashi-1, CD133, uPAR, and hGAPDH commercially available, pre-designed sets of primers were used (Invitrogen-ID is indicated for purchase information).

EXAMPLES

In the examples, tumor cells that would remain after surgery, i.e. tumor cells of the peripheral zone of the tumor, have been isolated and characterized in comparison with cells routinely found in the cores (centres) of tumor tissue. To demonstrate the method according to the invention, biopsies of patients suffering form glioblastoma multiforme (GBM) were provided. For example, paired biopsy samples were used, representing the glioblastoma centre and the glioblastoma periphery from a total of 30 patients. Histological evaluation revealed classic signs of a GBM in the centre biopsy specimens while tissue from the periphery exhibited characteristics of an infiltration zone. For controlled analysis we used defined in vitro conditions for isolation and expansion of cells from these paired biopsy samples. Our data indicate distinct region-specific distributions of key features of cellular malignancy, i.e. the content of stem cells, and the respective migratory and proliferative potential of cells vary significantly between tumor centre and periphery. Furthermore, FACS and qPCR analysis revealed a complementary expression of tumor cell surface antigens.

Example 1

Experimental Methodology

Figure 2:
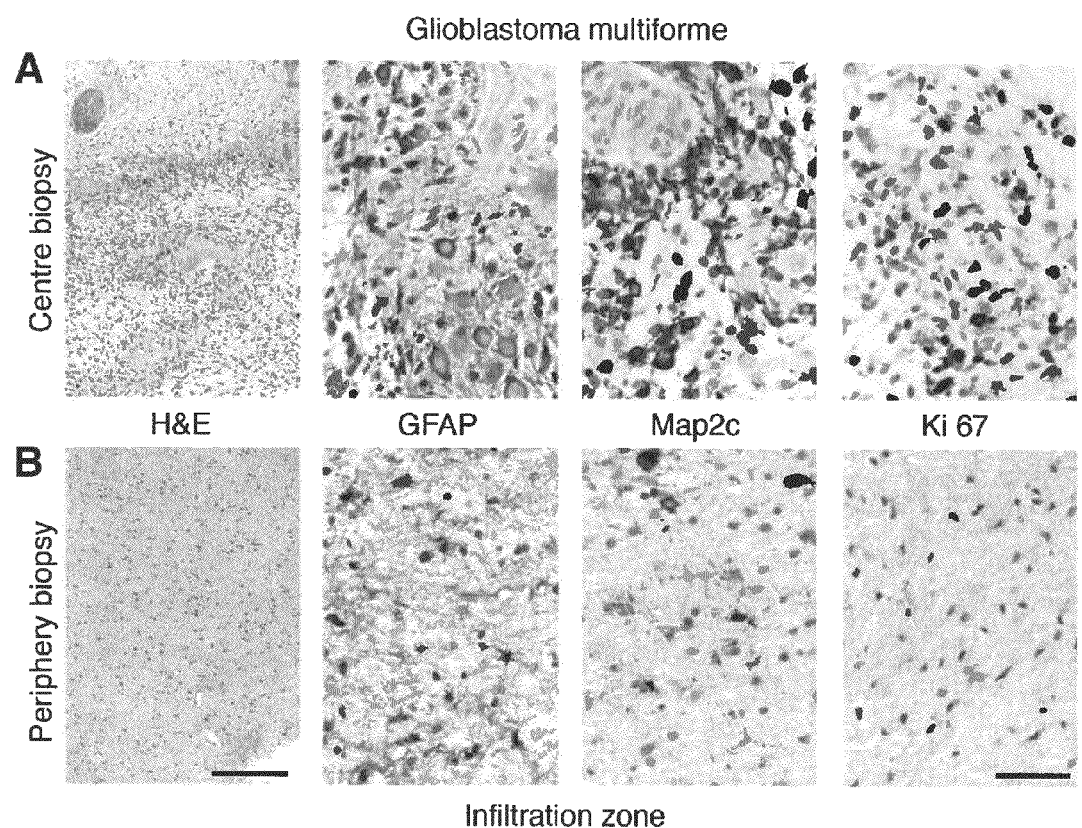
FIG. 2: Histological hallmarks of biopsy specimens. (A) This tissue sample (Patient 023) from a centre biopsy shows the criteria required for the diagnosis of a GBM: vascular proliferation and characteristic necrosis (H&E), pleomorphic glial tumor cells (GFAP, MAP2c), and an abundance of mitotic/proliferative activity (Ki 67). (B) Tissue from the same patient's periphery biopsy site exhibits signs commonly attributed to the infiltration zone (INF) of a malignant glioma: increased cellular density, abnormal grouping of cells and occasional mitotic figures (H&E). Furthermore, there is substantial reactive gliosis (GFAP) and a few tumor cells present (Map2c) that exhibit signs of increased proliferative activity (Ki 67). Note that for immunohistochemistry (GFAP/Map2c, Ki67), antigens were detected by standard DAB reaction (black). Scale bars: H&E, 200 µm; GFAP/Map2c/Ki67, 50 µm.

Tissue procurement and culture. The tumor tissue samples were provided from patients following informed consent through the Department of Neurosurgery, University of Bonn Medical Centre. The local ethics commission approved all procedures. The histological diagnosis of the samples was performed according to the current classification of World Health Organization (9) and confirmed by two independent neuropathologists at the Department of Neuropathology, University of Bonn Medical Centre (the National Reference Center for Neuropathology). Paired biopsy samples (each between 0.125-0.5 cm$^3$ in size) were received 30 to 60 minutes after removal and the tissues were subsequently dissected under sterile conditions into three representative fractions. One fraction was fixed with 4% paraformaldehyde (PFA) for histological analysis (see FIG. 2), the second fraction underwent snap freezing in liquid nitrogen for future molecular analysis, and the third fraction was used to prepare a single cell suspension using 0.25% trypsin and fire polished Pasteur pipettes. The single cell suspension was plated into non-adhesive culture conditions for immediate analysis (see FIG. 3), and/or into adhesive culture conditions for cell expansion in proliferative media (PROL; composition according to ref. 7). For non-adhesive culture conditions, 10$^4$ cells/cm$^2$ were plated into non-adherent 6-well culture dishes (Corning, Schiphol-Rijk, The Netherlands; #3471) in defined serum-free PROL media provided with 20 ng/ml EGF/bFGF (R&D systems, Minneapolis, USA). 10 ng/ml EGF/bFGF was then added every other day thereafter. For adhesive culture conditions cells were plated into 6 cm laminin/poly-L-ornithine coated plastic dishes (for method of cell culture dish coating, see ref. 28). 20 ng/ml EGF/bFGF was provided upon plating, and 10 ng/ml EGF/bFGF was then added every other day thereafter. The cells were propagated by serial passaging in ratios of 1:2 or 1:3 every 4-7 days and stocks of at least 2×10$^5$ cells/vial were frozen at passage 4. After thawing, the various experimental paradigms were conducted (see FIGS. 4-7, 10-12).

Immunocytochemistry. For each case, representative PFA-fixed tissue fragments (see above) were embedded in paraffin for the histological analysis that included H&E staining as well as automated immunocytochemistry (Tecan, Männerdorf, Switzerland; Genesis RSP 100) with antibodies against GFAP (DAKO, Glostrup, Denmark; polyclonal rabbit 1:500), Map2c (Sigma, Munich, Germany; monoclonal mouse, 1:1,000), p53 (DAKO, monoclonal mouse 1:100), and Ki67 (DAKO, monoclonal mouse, 1:50). Detection with appropriate secondary antibodies was visualized using the standardized DAB reaction. Immunofluorescence analysis of cultured cells was performed on 4% PFA-fixed samples according to standard protocols (see refs. 10 and 28) using antibodies against βIII tubulin (Covance, Berkeley, USA; monoclonal mouse, 1:1,000), CD133/2 (Miltenyi, Bergisch-Gladbach, Germany; monoclonal mouse, 1:11), CNPase (Chemicon, Temecula, USA; monoclonal mouse, 1:250, GFAP, and uPAR (American Diagnostica; Stanford, USA; monoclonal mouse, 10 µg/ml). Cell nuclei were visualized by labeling with 0.8 µ/ml DAPI (Sigma).

The standard neurosphere assay. The NSA (detailed method in ref. 10) was used for 10 cases of cells from periphery and centre biopsies at culture passage 5 (5-8 population doublings). Briefly, a single cell suspension of 10$^4$ cells/cm$^2$ was diluted in 1% methylcellulose-containing PROL media provided with 20 ng/ml EGF/bFGF, and inoculated into non-adhesive culture dishes. 10 ng/ml EGF/bFGF was then added every other day. At 21±4 days in culture (dic), NSs were quantified, and a single cell suspension was performed for plating and analysis of the formation of secondary or higher degree neurospheres under identical conditions. For analysis of multipotency, a representative fraction of 2° or 3° NSs was used. NSs were plated onto laminin/poly-L-ornithine coated glass coverslips (see ref. 10) and, after attachment, provided with PROL media devoid of mitogens to allow differentiation for 2-3 weeks in culture before PFA-fixation and immunofluorescence analysis (see above).

Proliferation kinetic. Expansion under defined conditions in PROL media (see above) was performed in eight cases of paired biopsies to determine the respective proliferative capacities. 1.25×10$^5$ cells were plated per sample into 6 cm laminin/poly-L-ornithine coated plastic dishes at passage 5 (for method of cell culture dish coating, see ref. 28). 20 ng EGF/bFGF were provided upon plating, and 10 ng EGF/bFGF were added every other day thereafter. Four-to-six days later, adherent cells were enzymatically digested (0.25% trypsin), harvested, and counted to plate a fraction of 1.25×10$^5$ cells into the next passage. This procedure was repeated until passage 10 or 11, and cell numbers were determined to calculate the population doublings (PD) according to Hayflick's formula: n=3.32 (log UCY–log I)+X (see ref. 29). The PD level was set to zero for all initially plated cells at passage 5 to enable comparative cross- and intra-case analysis. Slope analysis and statistics were performed using the Excel calculation program. The level of significance was set to $p<0.05$.

Migration analysis. Matrigel® invasion chambers (BD Biosciences, Bedford, USA) were used according to the manufacturer's advice for the analysis of the migratory competence of passage 5 cells from periphery and centre biopsy samples. For each sample investigated, 5×10$^4$ cells were inoculated into the upper chamber (onto the coated membrane) in PROL media. The lower chamber was provided with 10% fetal calf serum (FCS) in PROL media. After 44 hours of incubation in 37° C., 5% $CO_2$-saturated conditions, membranes were fixed with 4% paraformaldehyde for DAPI staining of nuclei (see above) and for subsequent quantification of migrated cells according to the manufacturers suggestions. To determine the ratio of migrated/invaded cells, two simultaneously inoculated chambers were needed per experiment and case: One chamber was used to count (non-invasive) cells on top of the membrane (by removing the cells from the bottom). The other chamber (freed of cells on top of the membrane) was investigated for the number of migratory/invasive cells. For each case, three independent rounds of experiments were performed.

FACS-Analysis. Passage 5 cells were trypsinized, collected at a density of 10$^6$ cells/ml, and incubated in 5% FCS-containing phosphate buffered saline (Invitrogen, Karlsruhe, Germany) with a direct conjugated antibody to the CD133/2 (APC or PE) epitope (1:11) according to the manufacturers suggestions (Miltenyi). To distinguish between living and dead cells, labeling with 1.2 µg/ml bisbenzimide H33258 (Invitrogen) was subsequently performed. The expression of CD 133/2 was determined by flow cytometry using standard conditions in a LSRII equipped with FACSDiva Software (BD Biosciences).

qRT-PCR Analysis. Quantification of mRNA was performed from passage 5 cells using the RNeasy kit according to the manufacturers suggestions (Qiagen, Hilden, Germany). cDNA was generated, and, real-time polymerase chain reaction was performed on an iCycler iQ multicolour real-time PCR detection system (Biorad, Munich, Germany) applying the Taqman detection protocol. Costum-made Lux-labeled primers (Invitrogen) were used to detect the expression of CD133 and uPAR in the samples, respectively. Specifically, the following FAM-labeled primers were used: (1) NM_002046 (hGAPDH), forward, cat#100H-01; (2) NM_006017 (CD133), forward, HLUX3013322; (3) NM_002659 (uPAR), forward, HLUX3008919. The mean normalized expression was calculated with the Qgene Pro software (Biorad) using the housekeeping gene hGAPDH as reference. All experiments were performed in triplicates for each sample.

Molecular analysis. Genotyping of 620,901 SNPs was conducted using the Illumina (USA) Human610-Quad BeadChip according to the manufacturer's Infinium II protocol. Chromosomal aberrations were identified by examination of log R ratios and B-allele frequencies. qRT-PCR analysis was performed on an iCycler iQ multicolour real-time PCR detection system (Biorad, Germany) applying standard Taqman or Sybr-green detection protocols. Costum-made or predesigned primers (Invitrogen) were used for transcript analysis (FIG. 13).

Statistics. For center vs. periphery comparison of mean values the Student's t-test (cell culture experiments) or the Wilcoxon signed-rank test (qRT-PCR data) were applied (SPSSv.17.0; level of significance set to $p<0.05$).

Single nucleotide polymorphism array analysis. For genome-wide single nucleotide polymorphism (SNP) analysis, DNA was isolated using the Qiagen AllPrep DNA/RNA Mini Kit (Qiagen, Hilden, Germany) following the manufacturer's instructions. Genotyping of 620,901 SNPs was conducted using the Illumina Human610-Quad BeadChip according to the manufacturer's Infinium II protocol (Illumina, San Diego, USA). Data were analyzed with Illumina BeadStudio (3.1.3) software including the Genotyping (3.3.4) and Genome Viewer (3.2.9) modules. Chromosomal aberrations were identified by examination of log R ratios and B-allele frequencies.

Fluorescence in situ hybridization (FISH)-analysis. 4 μm cryosections of tumor specimens and methanol/glacial acetic acid (3:1 v/v) fixed cell culture samples (passage 5 and 7) were used for FISH analysis. Sample treatment and application of FISH probes were performed as suggested by the manufacturer (for tissue analysis: MDM2, CDK4 and SE12, Kreatech, Amsterdam, The Netherlands). For cell culture sample analysis of interphase nuclei, bacterial artificial chromosome probes (kindly provided by the Department of Pathology, University of Bonn) were labeled with Spectrum Orange (RP11-797C20, MDM2 and RP11-571M6, CDK4; Bacpac, Oakland, Calif., USA) with a nick translation kit according to the manufacturer's protocol (Abbott, Wiesbaden, Germany). A control centromer 12 probe (CEP12, D12Z3; Abbott) labeled with Spectrum Green was included. Frequencies of aberrant cells were determined by examination of 100 nuclei. Experiments were performed in triplicates.

Treatment regimens. 24 hours after seeding $2-3\times10^3$ cells/well into laminin/poly-L-ornithine (see above) coated 96-well plates, primary cultures were treated with either 5 Gy ionizing irradiation (6-MeV medical linear accelerator Mevatron MD2, Siemens, Munich, Germany), temozolomide (TMZ, Sigma; stock solution of 100 mM in DMSO), lomustin (CCNU, medac, Wedel, Germany; stock solution of 38 mM in 20% EtOH), or combined irradiation and chemotherapy regimens (5 Gy+temozolomide or lomustine). TMZ and CCNU were diluted in PROL media to a final concentration of 500 μM and 380 μM, respectively. Control cells were treated with 0.5% DMSO or 0.2% EtOH. Five days after application, cell viability was determined using the alamarBlue® assay according to the manufacturers recommendations (Invitrogen). Absorbance was determined 6 hours after application of 10% alamarBlue® at 590 nm and 544 nm using a fluorescence microplate reader (GEMINI XS, Molecular Device, Ismaning, Germany). Experiments were performed in triplicates for each sample. 95%-confidence intervals were determined for every modality and sample. Non-overlapping confidence intervals of center vs. periphery cultures were considered as dissimilar response.

Example 2

Patient and Tissue Characterization

Figure 1:
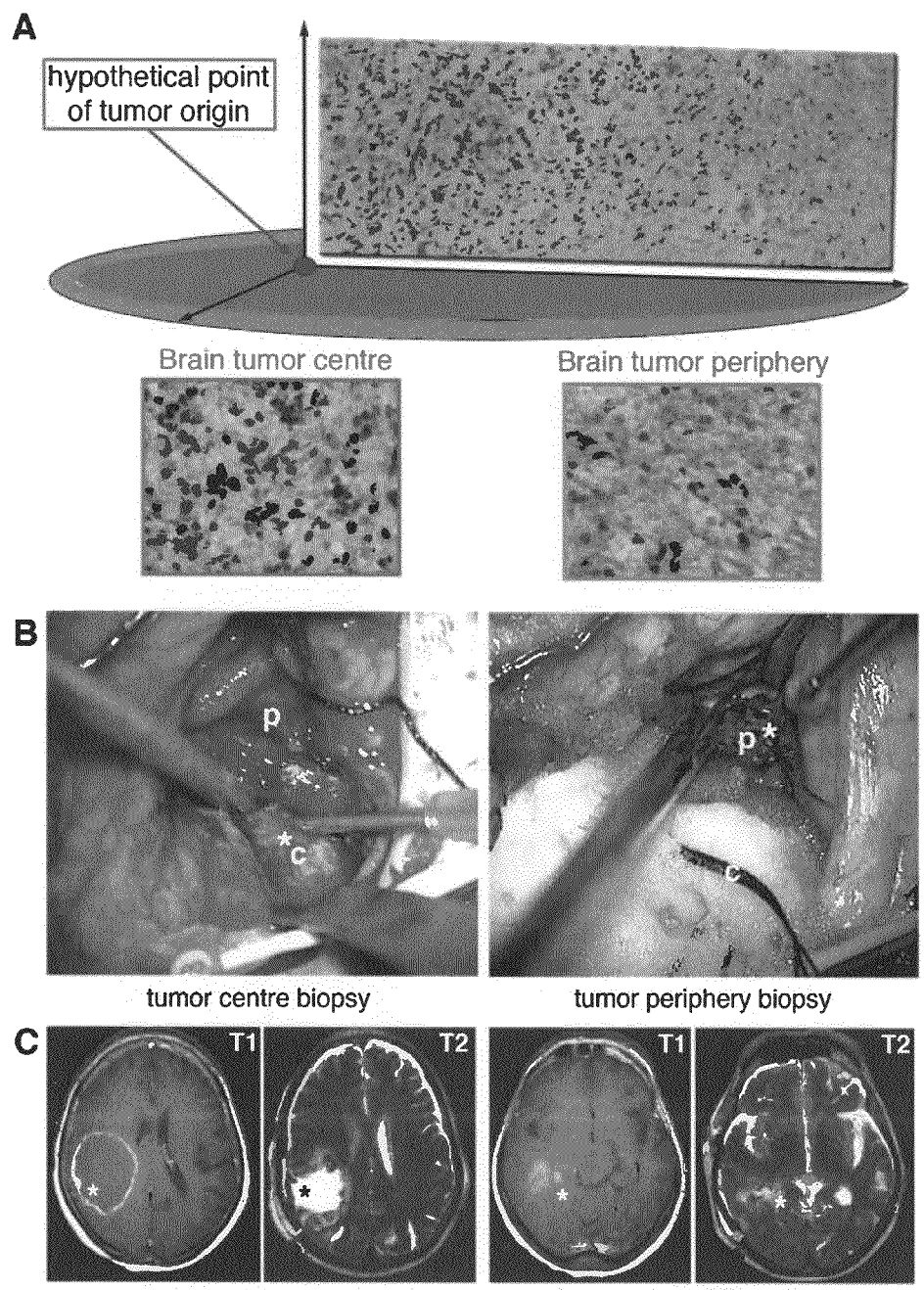
FIG. 1: Rationale and experimental design. (A) The cartoon visualizes a hypothetical brain tumor model exposing the point of origin in the tumor centre (grey), and the tumor periphery or infiltration zone (light grey, outer rim). Note that the display items in the cartoon highlight infiltrating glioblastoma cells by their abnormal accumulation of the p53 gene product (visualized by DAB reaction, black). (B) Macroscopic view of the surgery site. Two tissue specimens were obtained from each patient representing the tumor centre (c), and the periphery (p), respectively. (C) MRI analysis before (T1-weighted images) and after surgery (T2-weighted images) of the patient shown in (B) visualizes the experimental design applied: Tumor centre biopsy cells portray tumor tissue that is removed during standard neurosurgical procedure; cells from the periphery biopsy specimen embody characteristics of the infiltration zone. Note that the asterisks shown in (B) and (C) expose the exact regions of the biopsy taken.
Figure 8:
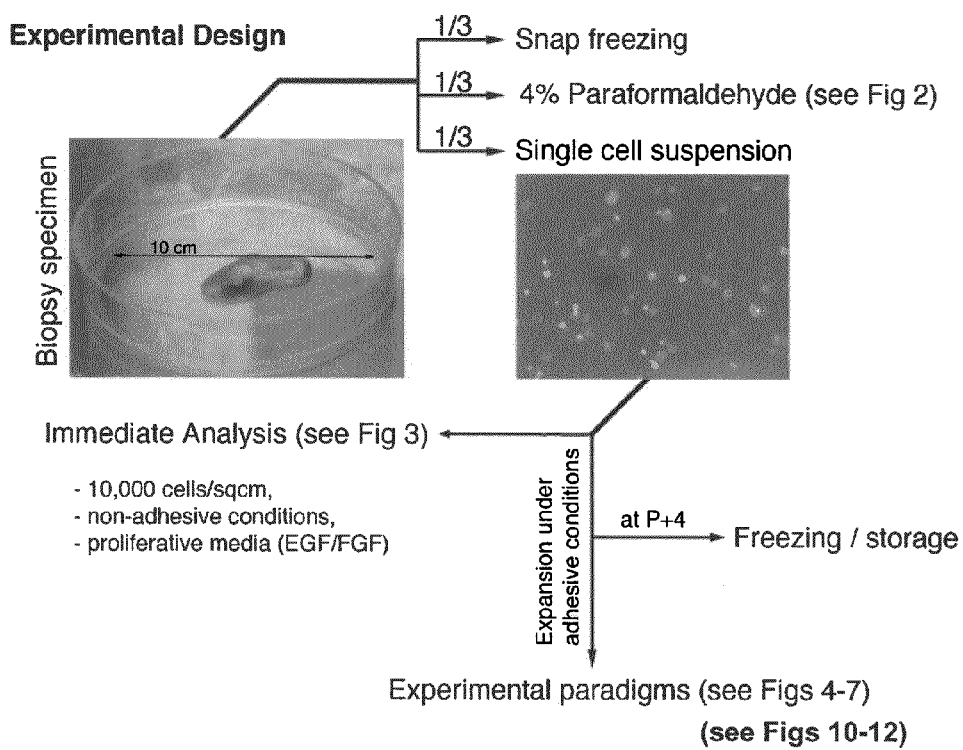
FIG. 8: Tissue procurement and culture. The flow chart describes the stepwise protocol applied in the examples.
Figure 10:
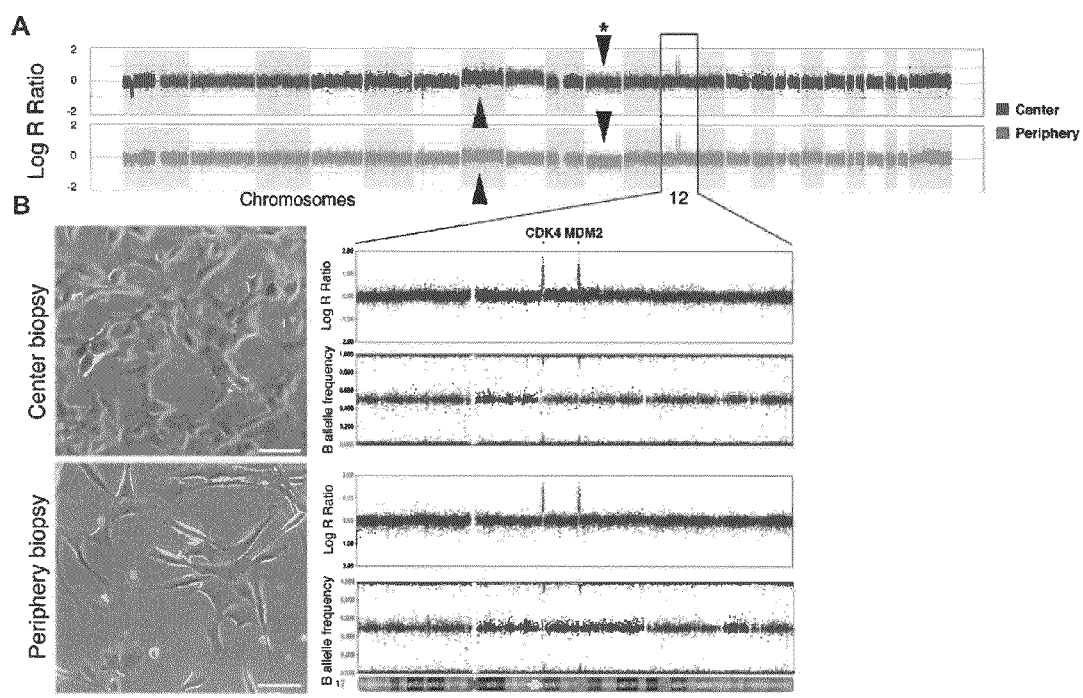
FIG. 10: Characterization of tumor tissue and primary cells. (A) SNP-based genotyping demonstrated largely overlapping profiles of GBM-typical alterations in paired cultures. In the presented case (patient #023), gain of chromosome 7 (arrowheads-up), loss of heterozygosity (LOH) chromosome 10 (arrowheads-down), and focal amplifications of CDK4 and MDM2 on chromosome 12 (boxed area) were noted. Always, however, minor genomic alterations distinguished paired cultures from each other. In the presented case, the detected chromosome 10 LOH was copy-neutral only in cells from the routinely resected tissue (asterisk in upper panel). (B) Phase contrast of the #023 primary cultures at passage-7 (left). SNP-genotyping data of chromosome 12 highlights the amplifications of the CDK4 and MDM2 loci used in this case to determine the frequency of patient-specific GBM cells in vitro and in vivo. (C) Fluorescence in situ hybridization (insets, specific gene probe in red; centromer probe chromosome 12 in green) revealed the presence and enrichment of patient-specific cells in vitro (top graph, center biopsy; bottom graph, periphery biopsy). Both alterations were present in 100 ($\pm$0) % of the cells from center and periphery cultures. (D) In contrast, the parental tissue revealed a frequency of only 73 ($\pm$1.3) % (center) (top graph) vs. 12 ($\pm$1.6) % (periphery) (bottom graph) MDM2-/CDK4-amplified tumor nuclei, respectively. Scale bars: (B)=30 μm; (C)=15 μm.
Figure 10:
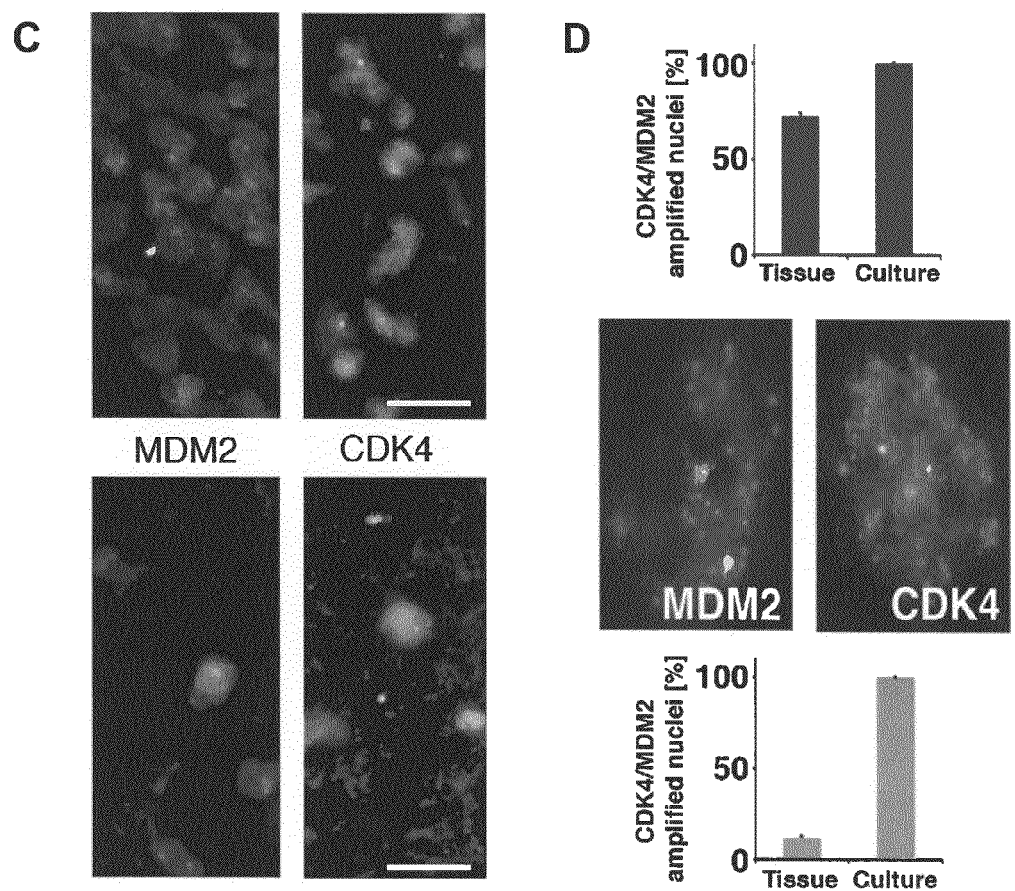

For analysis, two tissue specimens were obtained from each patient representing the tumor centre and the periphery of the malignancy, respectively (FIGS. 1B, C). Paired tissue samples were analyzed from 30 GBM patients (18 males, 12 females), between 27 and 79 years old at the time of surgery (FIGS. 8 and 9). Tissue samples derived from tumor centre biopsy, in general, displayed the neuropathological criteria required for the diagnosis of a GBM according to the current definition of the WHO (9). Characteristic findings included vascular proliferation and necrosis, the presence of pleomorphic glial tumor cells, and an abundance of mitotic/proliferative activity (FIG. 2A). In contrast, tissue from periphery biopsy sites exhibited signs commonly attributed to the infiltration zone of a malignant glioma (INF). In general, there was an increased cellular density with abnormal grouping of cells, and also, occasional mitotic figures were observed (FIG. 2B). Exclusive morphological characteristics of a GBM were found in 24/30 (80%) centre biopsy specimens, and exclusive characteristics of an INF were observed in 24/30 (80%) of the periphery biopsy samples. In a few instances, tissue samples contained mixtures of GBM and INF (11/60; 18%), and rarely, exclusive GBM qualities were observed in samples derived from periphery biopsy (1/30; 3%) (FIG. 9). The abundant presence of tumor cells in tissue from routine resection (GBM center) compared to sparsely distributed residual cells in tissue from the resection margin (GBM periphery; FIGS. 2A and B) indicated a need for isolation and enrichment of center and residual GBM cells for standardized comparisons on a functional level. For experimentation, we used recently suggested methods for in vitro derivation of primary GBM cultures that retain original tumor characteristics (Lee J, Kotliarova S, Kotliarov Y et al. Tumor stem cells derived from glioblastomas cultured in bFGF and EGF more closely mirror the phenotype and genotype of primary tumors than do serum-cultured cell lines. Cancer Cell. 2006; 9: 391-403). To verify this approach, and to investigate for a previously not demonstrated degree of tumor cell enrichment under these conditions, we examined passage 7+/−2 cells from a total of three paired tissue samples (#'s: 021, 023, 035; shown is #023). Genotype analysis confirmed that cells expanded from both tumor regions retained GBM-typical alterations (FIGS. 10A and B). Fluorescence in situ hybridization studies furthermore directly revealed a striking enrichment of tumor cells and patient-specificity in cultures from both tumor regions (FIGS. 10C and D). Thus, the subsequent comparative analysis of center and residual GBM populations was conducted between cell culture passages 5 and 10.

Example 3

Immediate in Vitro Analysis Reveals Distinct Topographic Growth Patterns

Single cell suspensions were prepared from the paired tissue samples, plated into non-adhesive culture dishes, and provided with mitogens for 14±4 days (see example 1). Under these conditions, cells from centre biopsy samples, in general, formed spherical structures while specimens from the tumor periphery appeared often less organized (FIG. 3A). However, viable cell counting at the end of the observation interval demonstrated overall comparable numbers of cells present in the periphery and the centre biopsy cultures (FIG. 3B). Thus, the distinct growth patterns and kinetics in this assay indicated significant biological differences between cells from the periphery versus centre biopsies. Because specifically, the presence of large quantities of cellular aggregates in centre biopsy cultures implied a substantial incidence of stem-like cells, we next applied a standard neurosphere assay (NSA; see example 1 and ref. 10) to quantify and expose the content of self-renewing and multipotent cells.

Example 4

The Nsa Reveals Characteristic Regional Distributions of Stem Cells in Gbm

The standard neurosphere assay (NSA) was applied to 11 cases (patients 013, 015, 016, 018, 021, 023, 025, 026, 035, 037 and 046) of expanded cells from periphery and centre biopsies at culture passage 5 (5-8 population doublings). In most cases, primary neurospheres (NS) arose under proliferative low-density conditions from periphery and centre biopsy cultures within 2-3 weeks in culture (FIG. 4A). The formation of secondary NSs was observed more infrequently (FIG. 4B). The mean data analysis of eleven pairs (patients 013, 015, 016, 018, 021, 023, 025, 026, 035, 037 and 046) of 1° NS, 2° NS and 3° NS culture stages revealed among GBM center cells a significantly higher ratio of continuously self-renewing (the attributed features of stem cells) cells ($*p<0.05$) (FIG. 4B). In line with these observations, quantitative RT-PCR analysis of neural stem/progenitor-typical transcripts (Bao S, Wu Q, McLendon R E et al. Glioma stem cells promote radioresistance by preferential activation of the DNA damage response, Nature, 2006; 444: 756-760) revealed significantly increased levels of Sox2 and Nestin as well as a trend for increased levels of Musashi-1 in GBM center cultures (mean data of the respective marker, ($*p<0.05$)) (FIG. 4D). Plating and differentiation of cells from individual 2° and 3° NSs always revealed the presence of GFAP-expressing astrocytes, βIII tubulin-expressing neurons, and CNPase⁺oligodendrocytes, suggesting multipotency of the respective NS-forming cells (FIG. 4C). These observations indicate that stem cell activity is predominantly confined to the centre biopsy specimens. Because the cells in the periphery that are likely implicated in glioma recurrence, we were next curious to determine the topography of other disease-specific biological hallmarks, i.e. the proliferative and migratory activities of cells from both regions (see below).

Example 5

Periphery Biopsy Cells Proliferate More Rapidly and Show a More Pronounced Migratory Activity Expansion of cells from eight paired biopsy samples was performed under adhesive conditions using defined media (see example 1) to determine and compare their proliferative capacity respectively. Individual cultures could be propagated at linear expansion rates without significant alterations to the cellular morphologies. However, in each case, we noted significant morphological differences between cells from the centre and the periphery samples (FIG. 5A). Slope analysis of the proliferation kinetics revealed a significant difference between slower proliferating centre and more rapidly expanding periphery biopsy-derived cultures (FIG. 5B). The Matrigel® invasion assay was furthermore used to determine the migratory competence of cells from representative paired biopsy samples (FIG. 6A). In this assay, all investigated primary cells showed a more pronounced migratory/invasive competence when compared to the U87 human glioma cell line used as a control. However, there was a topographic difference, with a significantly higher ratio of migratory active cells from periphery biopsy samples (FIG. 6B).

Example 6

Figure 7:
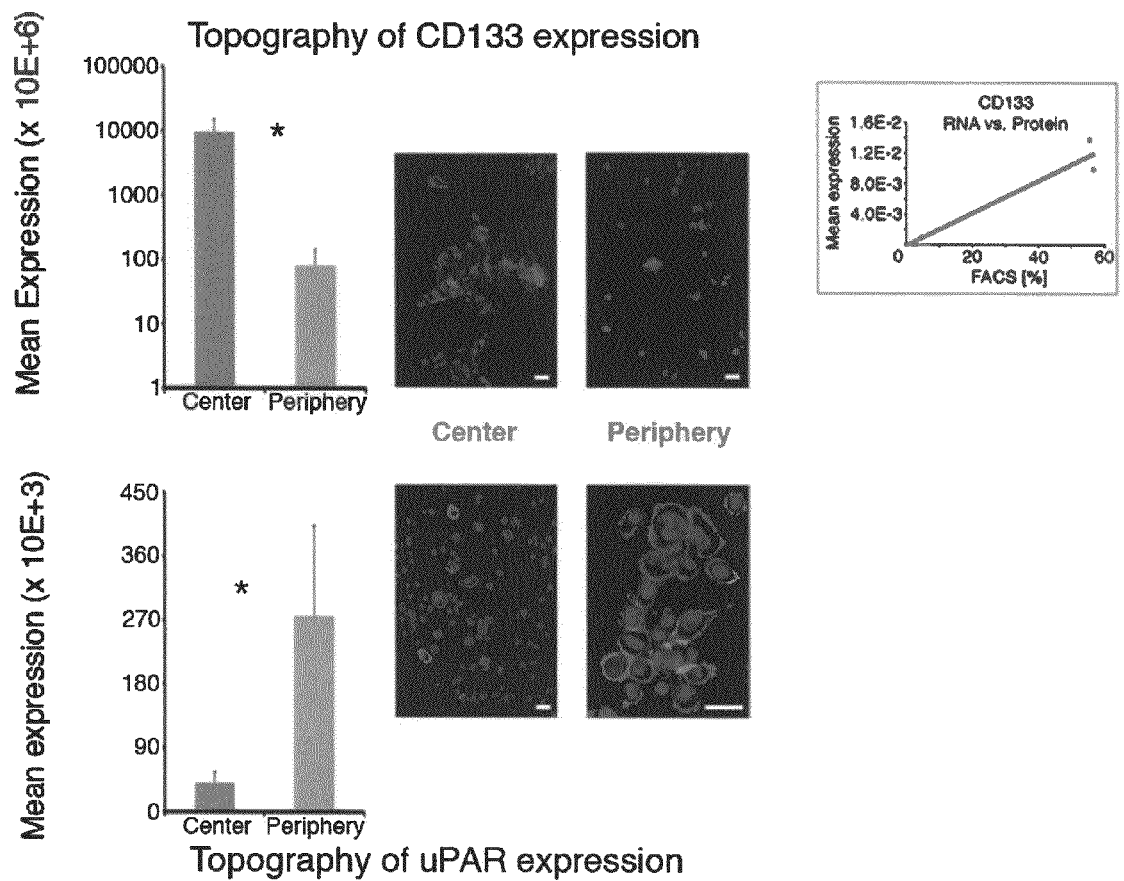
FIG. 7: Marker analysis and novel therapeutic targets. FACS and qPCR techniques were used to analyze CD133 and uPAR (CD87) expression. Culture samples of patients 013, 021, 023, 025, 035 and 046 at culture passage 5 were used. The coherence of qPCR data was verified with FACS analysis (see insert exemplarily for CD133). Direct comparison of CD133 and uPAR (CD87) expression levels reveals a distinct topographic pattern. High expression levels of CD133 and low levels of uPAR characterize cells from the centre biopsy, while cells from the periphery show a complementary pattern. The insets on the right show representative immunofluorescence photographs of CD133+ and uPAR+ cells. All columns in the graphs shown are paired, wherein each column pair consists of a left column referring to centre biopsy samples and a right column referring to periphery biopsy samples. Scale bars in the immunfluorescence photogrphs, 20 μm.

CD133 and Upar are Expressed in Complementary Patterns in Periphery and Centre Cultures FACS and qPCR techniques were used to validate the significant biological differences observed in cells from the periphery vs. centre regions of human GBM specimens. CD133, an epitope that can be found on cancerous stem cells (5, 6, 8), was observed in most samples derived from centre biopsies. CD133 was expressed to a significantly higher degree in the centre biopsy cells compared to the matching periphery samples (FIG. 7, upper panel). In contrast, uPAR was expressed at higher levels in cells derived from the periphery biopsy specimens (FIG. 7, lower panel). uPAR is the urokinase plasminogen activator receptor that was shown in several types of human cancer, including glioma to be correlated with increased cell growth, invasion and resistance to chemotherapy (11-15). The designation CD87 is synonymously used for uPAR. Taken together, direct comparison of CD133 and uPAR expression reveals a distinct topographic pattern: High levels of CD133 and low levels of uPAR characterize cells from the centre biopsy, and cells from the periphery show a complementary pattern (FIG. 7).

Example 7

VEGFR-2 and PDGFR-B are Expressed in Complementary Patterns in Periphery and Centre Cultures Intra-individual diversity of GBM center and residual cells was similarly revealed by expression analysis of molecular targets. The investigated markers revealed particularly distinguishing features of residual and center GBM cells: A complementary expression pattern was noted for VEGFR-2 (FIG. 11A) (significantly increased in center cultures) and PDGFR-B (FIG. 11B) (significantly increased in residual cells) ($*p<0.05$) like for CD133 (FIG. 7, upper panel) (significantly increased in center cultures) and uPAR (FIG. 7, lower panel) (significantly increased in residual cells).

Example 8

Cellular Responses of Center vs. Residual Cells to Radio-/chemotherapy

Figure 12:
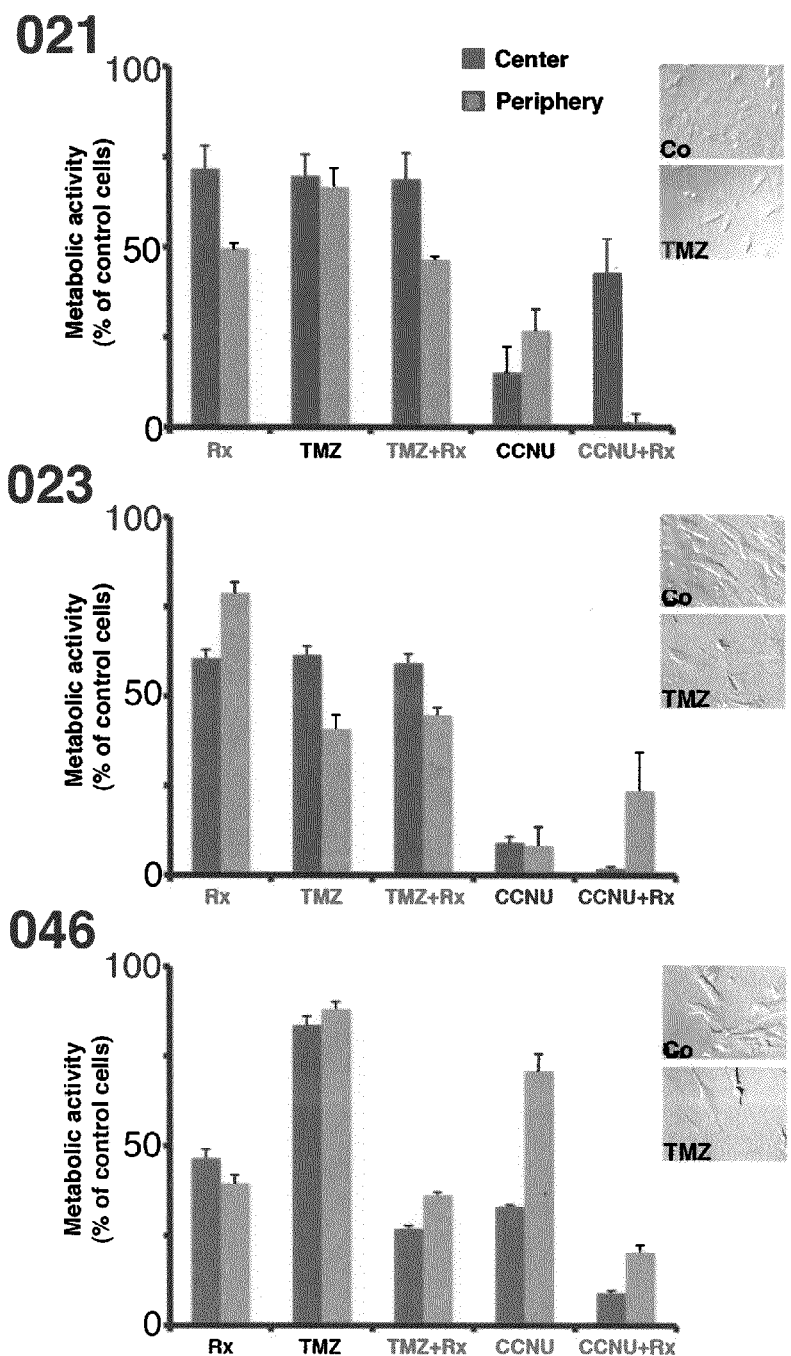
FIG. 12: Treatment sensitivity. Pairs of adherent passage-7 cells of patients 021, 023 and 046 were investigated in 96-well plates using standard/conventional treatment regimens. These included in vitro application of irradiation (Rx; 5 Gy), temozolomide (TMZ; 500 μM), lomustine (CCNU; 380 μM), and combinations thereof. Metabolic activity of cells was recorded five days after application using the alamarBlue® assay. Representative cell morphologies at the time of recording are presented as insets (differential interference contrast; Co=control/untreated; TMZ=temozolomide). Data showed that in 9/15 measurements, GBM periphery cells responded dissimilar (modalities indicated in grey; compared to black modalities) from the corresponding center cells. The columns in the graphs shown in FIG. 12 are paired, wherein each column pair consists of a left column referring to centre biopsy samples and a right column referring to periphery biopsy samples.

To determine if the distinct biological activities of center vs. residual cells could be of influence for therapeutic considerations, we tested cellular responses to radio-/chemotherapy, as well as the expression levels of prominent (pre-) clinical molecular targets (Sathornsumetee S, Reardon D A, Desjardins A et al. Molecularly targeted therapy for malignant glioma. Cancer. 2007; 110: 13-24; and Nakada M, Nakada S, Demuth T et al. Molecular targets of glioma invasion. Cell Mol Life Sci. 2007; 64: 458-478). Therapy response studies on three paired cell samples (#'s 021, 023, 046) were focused on current standard/conventional treatment modalities in clinical practice (Glas M, Happold C, Rieger J et al. Long-term survival of patients with glioblastoma treated with radiotherapy and lomustine plus temozolomide. J Clin Oncol. 2009; 27:1257-1261; and Stupp R, Mason WP, van den Bent M J et al. Radiotherapy plus concomitant and adjuvant temozolomide for glioblastoma. N Engl J Med. 2005; 352:987-996) and conducted as previously described (Beier D, Rohrl S, Pillai D R et al. Temozolomide preferentially depletes cancer stem cells in glioblastoma. Cancer Res. 2008; 68: 5706-5715; and Bao S, Wu Q, McLendon R E et al. Glioma stem cells promote radioresistance by preferential activation of the DNA damage response. Nature. 2006; 444: 756-760. We observed case-specific patterns of response to irradiation (Rx), temozolomide (TMZ), and CCNU, however, in 9/15 (60%) of all comparative measurements, residual cells responded dissimilar from their corresponding center GBM cells (FIG. 12).

Example 9

Conclusions

Figure 4:
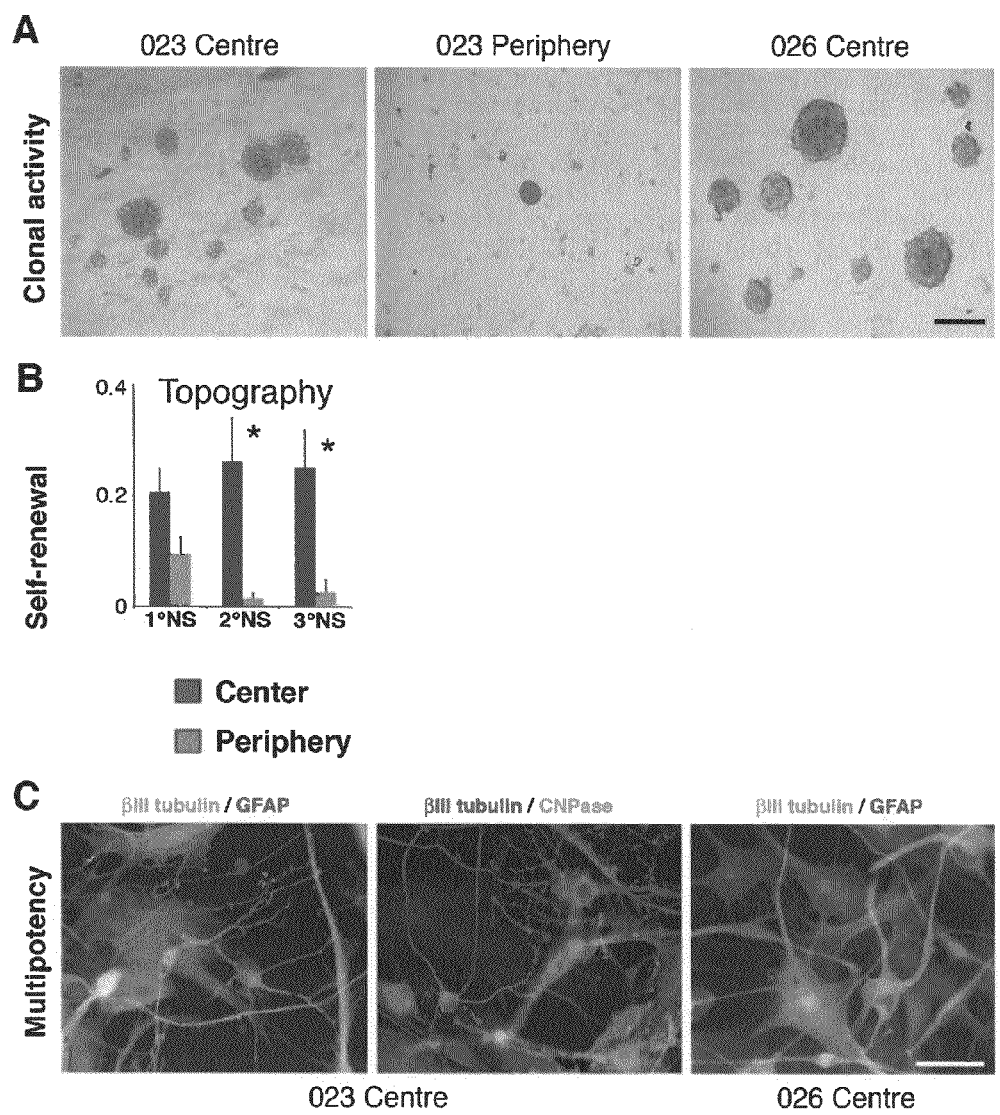
FIG. 4: Regional distribution of stem-like cells (Analysis of stem cells attributes in the neurosphere standard assay). The neurosphere standard assay (NSA) was applied to expanded cells from periphery and centre biopsies at culture passage 5. (A) Appearance of representative primary NSs at three weeks in culture. (B) In most cases, primary neurospheres (NSs) arose from periphery and centre biopsy cultures. The formation of secondary NSs was observed more infrequently. Mean data analysis of cells from 1°, 2° and 3° NSs (derived from the patients 013, 015, 016, 018, 021, 023, 025, 026, 035, 037, and 046) revealed among GBM center cells a significantly higher ratio of continuously self-renewing (stem) cells (*$p<0.05$). Each column pair consists of a left column referring to centre biopsy samples and a right column referring to periphery biopsy samples. (C) Plating and differentiation of cells from 2° and 3° NSs always revealed the presence of GFAP-expressing astrocytes, βIII tubulin-expressing neurons, and CNPase$^+$oligodendrocytes. Note that many NS-derived cells revealed phenotypes of so-called "asterons", indicated by their co-expression of GFAP and βIII tubulin (see ref. 30). (D) Quantitative RT-PCR mean data (patients 013, 016, 018, 021, 023, 025, 035, and 046) demonstrating the levels of neural stem/progenitor-typical transcripts Sox2, Nestin, and Musashi-1 (*$p<0.05$). For presentation in (D), mean data were multiplied with a factor of $10^4$. Each column pair consists of a left column referring to centre biopsy samples and a right column referring to periphery biopsy samples. Scale bars in (A), 200 µm; (C), 50 µm.
Figure 4:
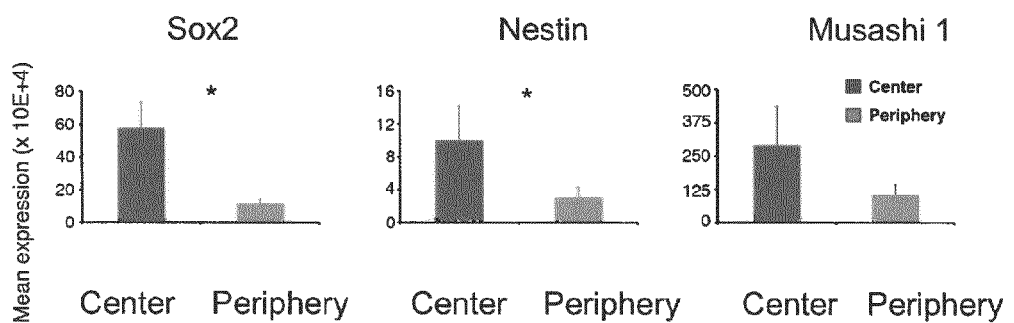
Figure 6:
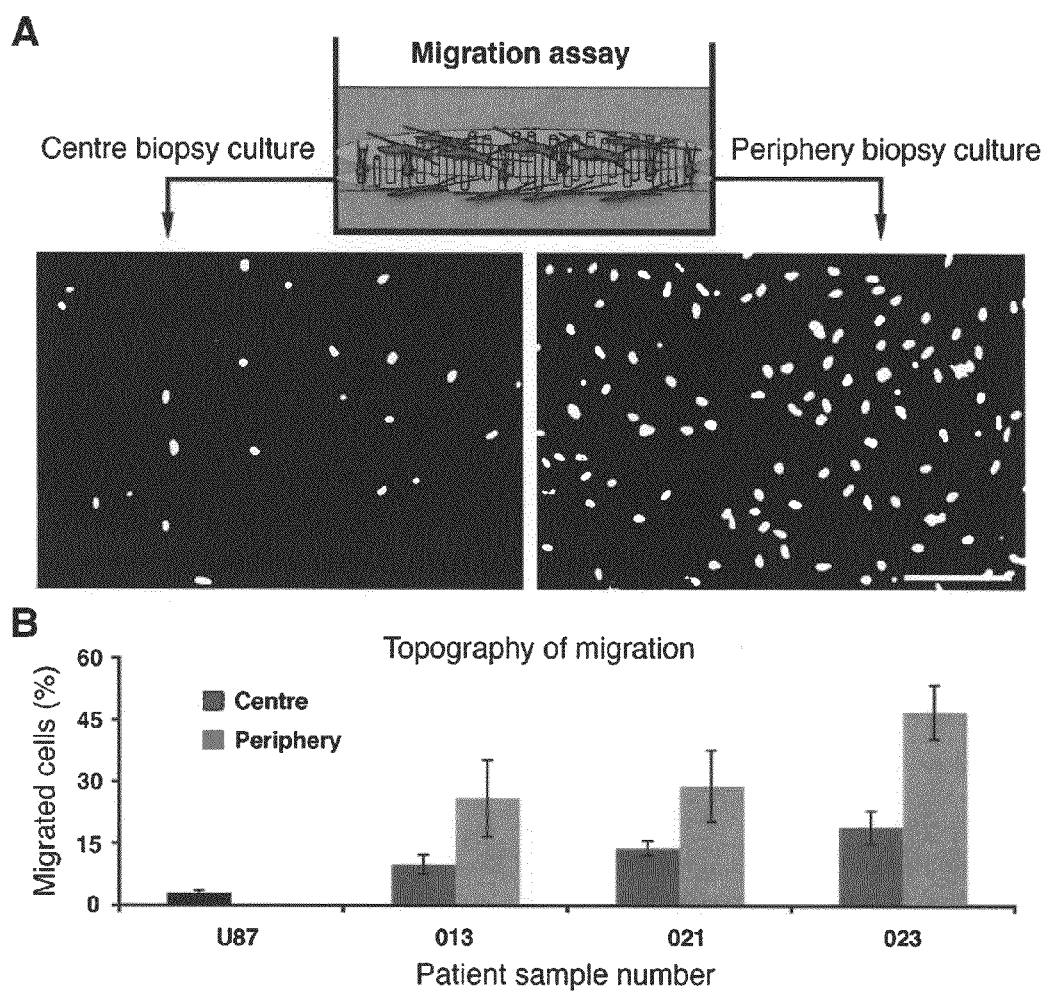
FIG. 6: Migration analysis. (A) The cartoon illustrates the migration assay based on chambers composed of an 8 µm pore-sized PET membrane, coated with a Matrigel® matrix. Non-invasive cells can be found on the matrix surface; migratory active cells on the bottom side. The photographs demonstrate DAPI-stained cell nuclei on the bottoms of the membranes (Patient 023). (B) Compared to the frequently used U87 human glioma cell line, all investigated patient-specific primary cells showed a more pronounced migratory/invasive competence. There was additionally a topographic difference, with a significantly higher ratio of migratory active cells present in periphery biopsy samples ($p<0.05$). The columns in the graph shown in (B) are paired, wherein each column pair consists of a left column referring to centre biopsy samples and a right column referring to periphery biopsy samples.

There are significant biological differences between cells derived from the GBM periphery and centre regions. Residual cells (for the studies described herein, residual GBM cells represent GBM periphery cells that were derived from the surgery site at the time of diagnosis and primary treatment) and cells found in routinely resected GBM tissue vary in their content of stem/progenitor cells, their proliferative and invasive capacity, their marker and molecular target profiles, and in their sensitivity to standard treatment regimens. Thus, it appears that residual cells represent distinct, malignant GBM sub-entities. These observations are important, as at least some of the cells from the periphery remain in the patient after standard surgery, and it is these cells that become exposed to adjuvant radio- and chemotherapy. These data indicate that cells with dissimilar characteristics from the primary manifestation that can be isolated e.g. from tissue of the recurrence are likely present already prior to standard therapy in distinct topographic arrangements. Thus, the ideal time to target and treat relapse-inducing glioblastoma cells could be the time of primary diagnosis. It may be of clinical importance to be able to distinguish glioma founder cells from cells responsible for the propagation and the recurrence of disease. In this regard, the present experimental results allow the comparison of cells from the origin site of the glioma (the tumor centre) with cells that reflect the ultimate location of the disease relapse (the tumor periphery). Recently, the involvement of stem cells has been proposed in the pathogenesis of GBM (18-20). Our results confirm the presence of clonogenic, self-renewing, and multipotent (stem) cells in almost every patient; yet, most frequently confined to the centre biopsy specimens (FIGS. 3, 4, and 7) and cells from the GBM periphery did rarely ever expose stem-like qualities (FIGS. 3 and 4). Regardless, our findings indicate that the cells in the tumor periphery possess stronger migratory and proliferative skills when directly compared to the cells derived from the GBM centre region (FIGS. 5 and 6). Based on the stem cell model of tumorgenesis (Visvader J E, Lindeman G J. Cancer stem cells in solid tumours: accumulating evidence and unresolved questions. Nat Rev Cancer. 2008; 8: 755-768), residual cells therefore fulfill the functional criteria of transit amplfifiers rather than to represent stem cells. Proliferation and invasion of tumor cells are good indicators for glioma malignancy, and determining these cellular features is integral part of the routine clinical diagnosis and the histological grading procedures (23). Even though the pathogenesis of human GBM is not entirely understood, the extensive migratory activity and the pronounced proliferative potential of tumor cells are classically viewed as at least in part responsible for the short time to progression (24, 25). Thus, cells originating from the GBM periphery will provide a valuable tool for analyzing the major drivers of the brain tumor's recurrence. This view is encouraged in our work by the showing of topographic dissimilarities of potential molecular targets (FIG. 7 and FIG. 11). Cells from the GBM periphery express to a significantly higher degree receptors for the urokinase plasminogen activator (uPAR/CD87). This receptor and the corresponding activator (uPA) are part of the regulatory machinery in cancer that enables individual tumor cells to degrade extracellular matrix, to migrate, and to invade surrounding tissue structures (27). Cells from the GBM pheriphery also express to a significantly higher degree the platelet-derived growth factor receptor B (PDGFR-B). The platelet-derived growth factor receptor B (PDGFR-B) has been recognized as important factor regulating cell proliferation, cellular differentiation, cell growth, development and many diseases including cancer. We also investigated if the distinct functional characteristics of residual GBM cells could influence current and potential future therapeutic considerations. Residual cells could be distinguished from GBM center cells in every case investigated here, by virtue of their distinct molecular marker profiles and by their distinct treatment responses. Our findings may be interpreted as representative for phenotypic tumor cell diversity, just as recently described for cells separated from different areas of the routinely resected GBM tissue (Piccirillo S G, Combi R, Cajola L et al. Distinct pools of cancer stem-like cells coexist within human glioblastomas and display different tumorigenicity and independent genomic evolution. Oncogene. 2009; 28: 1807-1811). However, in contrast to the latter study, we used residual GBM cells derived via experimental biopsy and enriched in vitro for controlled comparisons with cells from the routinely resected tumor tissue. On this basis, we were able to demonstrate functional similarities among residual GBM cells as well as a topographic distribution of specific cellular markers and putative therapeutic targets. Our study was performed on a limited number of cases; larger scale studies are warranted before profiling of GBM residual cells can be translated into routine clinical application. Nevertheless, comparative analysis of function, molecular markers, and treatment responses suggested that profiling of resected GBM tissue has only little value for predicting an intra-individual profile of residual cells. Thus, the revealing of distinct cellular and molecular properties in residual cells may be required for future diagnosis and treatment and should lead to a more comprehensive understanding of GBM pathology.

REFERENCES

1. Rao, J. S. 2003. Molecular mechanisms of glioma invasiveness: the role of proteases. Nat Rev Cancer. 3:489-501.
2. Mitchell, P., Ellison, D. W., Mendelow, A. D. 2005. Surgery for malignant gliomas: mechanistic reasoning and slippery statistics. Lancet Neurol. 4:413-22.
3. Stummer, W., Pichlmeier, U., Meinel, T., Wiestler, O. D., Zanella, F., Reulen, H. J.; ALA-Glioma Study Group. 2006. Fluorescence-guided surgery with 5-aminolevulinic acid for resection of malignant glioma: a randomised controlled multicentre phase III trial. Lancet Oncol. 7:392-401.
4. Stupp, R., Mason, W. P., van den Bent, M. J., Weller, M., Fisher, B., Taphoorn, M. J., Belanger, K., Brandes, A. A., Marosi, C., Bogdahn, U., Curschmann, J., Janzer, R. C., Ludwin, S. K., Gorlia, T., Allgeier, A., Lacombe, D., Cairncross, J. G., Eisenhauer, E., Mirimanoff, R. O.; European Organisation for Research and Treatment of Cancer Brain Tumor and Radiotherapy Groups; National Cancer Institute of Canada Clinical Trials Group. 2005. Radiotherapy plus concomitant and adjuvant temozolomide for glioblastoma. *N Engl J Med*. 352:987-996.

5. Singh, S. K., Hawkins, C., Clarke, I. D., Squire, J. A., Bayani, J., Hide, T., Henkelman, R. M., Cusimano, M. D., Dirks, P. B. 2004. Identification of human brain tumour initiating cells. *Nature*. 432:396-401.

6. Bao, S., Wu, Q., McLendon, R. E., Hao, Y., Shi, Q., Hjelmeland, A. B., Dewhirst, M. W., Bigner, D. D., Rich, J. N. 2006. Glioma stem cells promote radioresistance by preferential activation of the DNA damage response. *Nature*. 444:756-760.

7. Lee, J., Kotliarova, S., Kotliarov, Y., Li, A., Su, Q., Donin, N. M., Pastorino, S., Purow, B. W., Christopher, N., Zhang, W., Park, J. K., Fine, H. A. 2006. Tumor stem cells derived from glioblastomas cultured in bFGF and EGF more closely mirror the phenotype and genotype of primary tumors than do serum-cultured cell lines. *Cancer Cell*. 9:391-403.

8. Piccirillo, S. G., Reynolds, B. A., Zanetti, N., Lamorte, G., Binda, E., Broggi, G., Brem, H., Olivi, A., Dimeco, F., Vescovi, A. L. 2006. Bone morphogenetic proteins inhibit the tumorigenic potential of human brain tumour-initiating cells. *Nature*. 444:761-765.

9. Louis, D. N., Ohgaki, H., Wiestler, O. D., Cavenee, W. K., Burger, P. C., Jouvet, A., Scheithauer, B. W., Kleihues, P. 2007. The 2007 WHO classification of tumours of the central nervous system. *Acta Neuropathol*. 114:97-109.

10. Scheffler, B., Walton, N. M., Lin, D. D., Goetz, A. K., Enikolopov, G., Roper, S. N., Steindler, D. A. 2005. Phenotypic and functional characterization of adult brain neuropoiesis. *Proc. Natl. Acad. Sci. USA*. 102:9353-9358.

11. Gondi, C. S., Lakka, S. S., Yanamandra, N., Olivero, W. C., Dinh, D. H., Gujrati, M., Tung, C. H., Weissleder, R., Rao, J. S. 2004. Adenovirus-mediated expression of antisense urokinase plasminogen activator receptor and antisense cathepsin B inhibits tumor growth, invasion, and angiogenesis in gliomas. *Cancer Res*. 64:4069-4077.

12. Meng, S., Tripathy, D., Shete, S., Ashfaq, R., Saboorian, H., Haley, B., Frenkel, E., Euhus, D., Leitch, M., Osborne, C., Clifford, E., Perkins, S., Beitsch, P., Khan, A., Morrison, L., Herlyn, D., Terstappen, L. W., Lane, N., Wang, J., Uhr, J. 2006. uPAR and HER-2 gene status in individual breast cancer cells from blood and tissues. *Proc. Natl. Acad. Sci. USA*. 103:17361-17365.

13. Gutova, M., Najbauer, J., Gevorgyan, A., Metz, M. Z., Weng, Y., Shih, C. C., Aboody, K. S. 2007. Identification of uPAR-positive chemoresistant cells in small cell lung cancer. *PLoS ONE*. 2:e243.

14. Lee, E. J., Whang, J. H., Jeon, N. K., Kim, J. 2007. The epidermal growth factor receptor tyrosine kinase inhibitor ZD1839 (Iressa) suppresses proliferation and invasion of human oral squamous carcinoma cells via p53 independent and MMP, uPAR dependent mechanism. *Ann. N.Y. Acad. Sci*. 1095:113-28.

15. Pillay, V., Dass, C. R., Choong, P. F. 2007. The urokinase plasminogen activator receptor as a gene therapy target for cancer. *Trends Biotechnol*. 25:33-9.

16. Spiegl-Kreinecker, S., Pirker, C., Marosi, C., Buchroithner, J., Pichler, J., Silye, R., Fischer, J., Micksche, M., Berger, W. 2007. Dynamics of chemosensitivity and chromosomal instability in recurrent glioblastoma. *Br. J. Cancer*. 96:960-969.

17. Wiewrodt, D., Nagel, G., Dreimüller, N., Hundsberger, T., Perneczky, A., Kaina, B. 2008. MGMT in primary and recurrent human glioblastomas after radiation and chemotherapy and comparison with p53 status and clinical outcome. *Int. J. Cancer*. 122:1391-1399.

18. Ignatova, T. N., Kukekov, V. G., Laywell, E. D., Suslov, O. N., Vrionis, F. D., Steindler, D. A. 2002. Human cortical glial tumors contain neural stem-like cells expressing astroglial and neuronal markers in vitro. *Glia*. 39:193-206.

19. Singh, S. K., Clarke, I. D., Terasaki, M., Bonn, V. E., Hawkins, C., Squire, J., Dirks, P. B. 2003. Identification of a cancer stem cell in human brain tumors. *Cancer Res*. 63:5821-5828.

20. Galli, R., Binda, E., Orfanelli, U., Cipelletti, B., Gritti, A., De Vitis, S., Fiocco, R., Foroni, C., Dimeco, F., Vescovi, A. 2004. Isolation and characterization of tumorigenic, stem-like neural precursors from human glioblastoma. *Cancer Res*. 64:7011-7021.

21. Zhu, Y., Guignard, F., Zhao, D., Liu, L., Burns, D. K., Mason, R. P., Messing, A., Parada, L. F. 2005. Early inactivation of p53 tumor suppressor gene cooperating with NF1 loss induces malignant astrocytoma. *Cancer Cell*. 8:119-130.

22. Jackson, E. L., Garcia-Verdugo, J. M., Gil-Perotin, S., Roy, M., Quinones-Hinojosa, A., VandenBerg, S., Alvarez-Buylla, A. 2006. PDGFR alpha-positive B cells are neural stem cells in the adult SVZ that form glioma-like growths in response to increased PDGF signaling. *Neuron*. 51:187-199.

23. Furnari, F. B., Fenton, T., Bachoo, R. M., Mukasa, A., Stommel, J. M., Stegh, A., Hahn, W. C., Ligon, K. L., Louis, D. N., Brennan, C., Chin, L., DePinho, R. A., Cavenee, W. K. 2007. Malignant astrocytic glioma: genetics, biology, and paths to treatment. *Genes Dev*. 21:2683-2710.

24. Matsukado, Y., Maccarty, C. S., Kernohan, J. W. 1961. The growth of glioblastoma multiforme (astrocytomas, grades 3 and 4) in neurosurgical practice. *J. Neurosurg*. 18:636-644.

25. Pietsch, T., Wiestler, O. D. 1997. Molecular neuropathology of astrocytic brain tumors. *J. Neurooncol*. 35:211-222.

26. Gondi, C. S., Lakka, S. S., Yanamandra, N., Siddique, K., Dinh, D. H., Olivero, W. C., Gujrati, M., Rao, J. S. 2003. Expression of antisense uPAR and antisense uPA from a bicistronic adenoviral construct inhibits glioma cell invasion, tumor growth, and angiogenesis. *Oncogene*. 22:5967-5975.

27. Blasi, F., Carmeliet, P. 2002. uPAR: a versatile signalling orchestrator. *Nat. Rev. Mol. Cell Biol*. 3:932-943.

28. Goetz, A. K., Scheffler, B., Chen, H. X., Wang, S., Suslov, O., Xiang, H., Brüstle, O., Roper, S. N., Steindler, D. A. 2006. Temporally restricted substrate interactions direct fate and specification of neural precursors derived from embryonic stem cells. *Proc. Natl. Acad. Sci. USA*. 103: 11063-11068. 6

29. Hayflick, L. 1973. Subculturing human diploid fibroblast cultures. In *Tissue Culture Methods and Applications*. P. F. Kruse Jr. And M. K. Patterson Jr., editors. Academic Press Inc., New York, USA. 220-223.

30. Laywell, E. D., Kearns, S. M., Zheng, T., Chen, K. A., Deng, J., Chen, H. X., Roper, S. N., Steindler, D. A. 2005. Neuron-to-astrocyte transition: phenotypic fluidity and the formation of hybrid asterons in differentiating neurospheres. *J. Comp. Neurol*. 493:321-33.

The invention claimed is:

1. A method for providing a brain tumor cell comprising the steps:
   (a) providing one cell or several cells of a first biopsy of a brain tumor centre;
   (b) providing cells of a second biopsy of peripheral zone tissue surrounding the tumor centre in step (a);
   (c) determining the concentration or the average concentration of the protein and/or the mRNA of the cellular marker CD133 and/or the cellular marker CD87 in the one cell or in the several cells provided in step (a);
   (d) determining the concentration of the protein and/or the mRNA of the cellular marker CD133 and/or the cellular marker CD87 in the cells provided in step (b);
   (e) selecting a brain tumor cell from the cells provided in step (b), wherein the selected tumor cell has at least one of the following features:
      (i) the selected brain tumor cell expresses the protein and/or the mRNA of the cellular marker CD133 in a concentration which is lower than the concentration or the average concentration of this marker in the one cell or in the several cells provided in step (a), respectively;
      (ii) the selected brain tumor cell expresses the protein and/or the mRNA of the cellular marker CD87 in a concentration which is higher than the concentration or the average concentration of this marker in the one cell or in the several cells provided in step (a), respectively;
      wherein the cells provided in step (b) do not comprise cells which are located less than 2 mm away from the surface of the tumor centre in step (a).

2. The method according to claim 1, wherein the first brain tumor centre and the second brain tumor periphery biopsy were obtained during the same surgical procedure.

3. The method according to claim 1, wherein the second biopsy was obtained at a later time point, in a second surgical procedure after the tumor centre had been removed in an earlier first surgical procedure.

4. The method according to claim 1, wherein in step (a) and/or in step (b) at least one cell is expanded in vitro using cell culture methodology prior to step (e).

5. The method according to claim 1, wherein the brain tumor centre of step (a) comprises a larger number of stem cells per unit volume of tissue than are comprised in the biopsy of the peripheral zone tissue of step (b).

6. The method according to claim 5, wherein the stem cells express at east one cellular marker selected from the group consisting of Nestin, Stat3, Kit, Sox1, Sox2, Msi1, Notch1, Melk, Pax6, CD44, BMI1, CD133, GFAP, SSEA-1, and PDGFRα.

7. The method according to claim 5, wherein the stem cells are multipotent stem cells that are capable of differentiating into astrocytes expressing GFAP, neurons expressing betaIII-tubulin and/or oligodendrocytes expressing CNPase.

8. The method according to claim 6, wherein the stem cells are multipotent stem cells that are capable of differentiating into astrocytes expressing GFAP, neurons expressing betaIII-tubulin and/or oligodendrocytes expressing CNPase.

9. The method according claim 5, wherein the stem cell is capable of growing into a spherical cell aggregate when cultured in cell culture.

10. The method according to claim 1, wherein the peripheral zone is characterized by an average tumor cell density of between 1 and 30 tumor cells per 100 healthy, non-tumor cells.

11. The method according to claim 1, wherein the first biopsy is derived from a tumor centre which comprises an average tumor cell density of at least 50 tumor cells per 100 healthy, non-tumor cells.

12. The method according to claim 1, wherein the first biopsy is derived from a tumor of a tissue selected from the group consisting of lip, oral cavity tissue, skin, blood and/or hematopoietic system, pharynx, digestive system, a gland, a tissue of the respiratory system, bone, articular cartilage, skin, connective tissue, a tissue of the urogenital area, of the nervous system and of the endocrine system.

13. The method according to claim 12, wherein the tumor of the nervous system is a WHO-grade I, II, III, or IV glioma of the brain.

14. The method according to claim 1, wherein the first biopsy comprises a larger number of cells per unit volume of tissue that express at least one of the proteins and/or mRNAs selected from the group consisting of GFAP, Map2c and Ki-67, than the number of cells comprised in the biopsy of the peripheral zone tissue of step (b).

15. The method according to claim 1, wherein the selected tumor cell additionally has at least one of the following features:
   (iii) the selected brain tumor cell expresses the protein and/or the mRNA of the cellular marker VEGFR-2 in a concentration which is lower than the concentration or the average concentration of this marker in the one cell or in the several cells provided in step (a), respectively;
   (iv) the selected brain tumor cell expresses the protein and/or the mRNA of the cellular marker PDGFR-B in a concentration which is higher than the concentration or the average concentration of this marker in the one cell or in the several cells provided in step (a), respectively;
   (v) the cell division rate of the selected brain tumor cell is greater than the cell division rate or the average cell division rate of the one cell or of the several cells provided in step (a), respectively; and/or
   (vi) the cell motility of the selected brain tumor cell is greater than the cell motility or the average cell motility of the one cell or of the several cells provided in step (a), respectively.

16. A method for identifying a therapeutic compound effective against a metastatic or infiltrative brain cancer disease comprising the steps:
   (a) contacting an isolated expanded brain tumor cell composition with a test compound wherein at least 60% of the cells comprised in said isolated expanded brain tumor cell composition express the protein and/or mRNA of the cellular markers CD87 and/or PDGFR-B, wherein the expanded cells comprised therein are derived from the peripheral zone surrounding a tumor centre wherein the cell composition does not comprise cells which are located less than 2 mm away from the surface of the tumor centre and wherein the cells which express the cellular markers CD87 and/or PDGFR-B;
      (i) express the cellular marker CD87 in a concentration which is higher than the average concentration of this marker in said tumor centre; and/or
      (ii) express the cellular marker PDGFR-B in a concentration which is higher than the average concentration of this marker in said tumor centre;
   (b) determining the cytotoxic activity of the test compound and/or determining the cytostatic activity of the test compound and/or measuring cell differentiation of the tumor cell upon contact with the test compound;

wherein the cytotoxic activity of the test compound is determined by using the alamarBlue® assay, by using alanyl-alanylphenylalanyl-aminoluciferin or by measuring apoptosis markers;

wherein the cytostatic activity of the test compound is determined by using dyes which label the DNA content of the cells;

wherein cell differentiation of the tumor cell is measured by measuring the expression of CD133 and/or CD87 in the tumor cell, wherein a loss of the expression of CD133 and/or CD87 indicates that said test compound effected a tumor cell differentiation; and (c) selecting a test compound as the therapeutic compound which is cytotoxic, cytostatic for said expanded tumor cells or said expanded tumor cell composition and/or induces cell differentiation of said expanded tumor cells or said expanded tumor cell composition.

17. A method for identifying a therapeutic compound effective against a metastatic or infiltrative brain cancer disease comprising the steps:

(a) contacting an isolated expanded brain tumor cell composition with a test compound wherein at least 60% of the cells comprised in said isolated expanded brain tumor cell composition express the protein and/or mRNA of the cellular markers CD87 and/or PDGFR-B, wherein the expanded cells comprised therein are derived from the peripheral zone surrounding a tumor centre wherein the cell composition does not comprise cells which are located less than 2 mm away from the surface of the tumor centre and wherein the cells which express the cellular markers CD87 and/or PDGFR-B;
and (i) express the cellular marker CD87 in a concentration which is higher than the average concentration of this marker in said tumor centre; and/or (ii) express the cellular marker PDGFR-B in a concentration which is higher than the average concentration of this marker in said tumor centre;

(b) determining the cytotoxic activity of the test compound and/or determining the cytostatic activity of the test compound and/or measuring cell differentiation of the tumor cell upon contact with the test compound;

wherein the cytotoxic activity of the test compound is determined by using the alamarBlue® assay, by using alanyl-alanylphenylalanyl-aminoluciferin or by measuring apoptosis markers;

wherein the cytostatic activity of the test compound is determined by using dyes which label the DNA content of the cells;

wherein cell differentiation of the tumor cell is measured by measuring the expression of CD133 and/or CD87 in the tumor cell, wherein a loss of the expression of CD133 and/or CD87 indicates that said test compound effected a tumor cell differentiation; and (c) selecting a test compound as the therapeutic compound which has at least one of the following properties:

(i) it is more cytotoxic for said expanded tumor cell than for a healthy, non-tumor cell;

(ii) it is more cytostatic for said expanded tumor cell than for a healthy, non-tumor cell; and/or (iii) it induces cell differentiation of said expanded tumor cell.

18. A method for identifying a molecular marker diagnostic for an infiltrative brain cancer comprising the steps:

(a) providing at least one isolated expanded brain tumor cell, wherein (1) said isolated expanded brain tumor cell is obtainable by a method according to claim 4, or (2) said isolated expanded brain tumor cell expresses the protein and/or the mRNA of the cellular markers CD133, CD87, VEGFR-2 and/or PDGFR-B, wherein the cell is derived from the peripheral zone surrounding a tumor centre located at least 2 mm away from the surface of the tumor centre, and wherein the cell (i) expresses the cellular marker CD133 in a concentration which is lower than the average concentration of this marker in said tumor centre;

(ii) expresses the cellular marker CD87 in a concentration which is higher than the average concentration of this marker in said tumor centre;

(iii) expresses the cellular marker VEGFR-2 in a concentration which is lower than the average concentration of this marker in said tumor centre; and/or (iv) expresses the cellular marker PDGFR-B in a concentration which is higher than the average concentration of this marker in said tumor centre;

(b) providing at least one cell of the tumor centre, the peripheral zone of which said tumor cell of step (a) was obtained from;

(c) determining the concentration of a molecule in the at least one tumor cell provided in step (a);

(d) determining the concentration of said molecule in the at least one cell provided in step (b); and (e) selecting, as the molecular marker, a molecule which (i) is present in the at least one tumor cell provided in step (a) but not in the at least one cell provided in step (b); or)

(ii) is present in the at least one tumor cell provided in step (a) and in the at least one cell provided in step (b) but wherein the molecular marker in the at least one tumor cell provided in step (a) is present at a concentration which is at least 50% higher or at least 50% lower than the concentration of said marker in the at least one cell provided in step (b), wherein the cells provided in step (b) do not comprise cells which are located less than 2 mm away from the surface of the tumor centre in step (a).

19. The method according to claim 18, wherein the molecular marker is present at a higher concentration in the at least one cell provided in step (a) than the at least one cell provided in step (b).

20. An isolated expanded brain tumor cell composition, wherein at least 60% of the cells comprised therein express the protein and/or the mRNA of the cellular markers CD87 and/or PDGFR-B, wherein the expanded cells comprised therein are derived from the peripheral zone surrounding a tumor centre wherein the cell composition does not comprise cells which are located less that 2 mm away from the surface of the tumor centre and wherein the cells which express the cellular markers CD87 and/or PDGFR-B (i) express the cellular marker CD87 in a concentration which is higher than the average concentration of this marker in said tumor centre; and/or (ii) express the cellular marker PDGFR-B in a concentration which is higher than the average concentration of this marker in said tumor centre;

wherein the expanded cells further (iii) express the cellular marker CD133 in a concentration which is lower than the average concentration of this marker in said tumor centre; and/or (iv) express the cellular marker VEGFR-2 in a concentration which is lower than the average concentration of this marker in said tumor centre.

21. An isolated expanded brain tumor cell composition, wherein at least 60% of the cells comprised therein express the protein and/or mRNA of the cellular markers CD87 and/or PDGFR-B, wherein the expanded cells comprised therein are derived from the peripheral zone surrounding a tumor centre wherein the cell composition does not comprise cells which are located less than 2 mm away from the surface of the tumor centre and wherein the cells which express the cellular markers CD87 and/or PDGFR-B
- (i) express the cellular marker CD87 in a concentration which is higher than the average concentration of this marker in said tumor centre; and/or
- (ii) express the cellular marker PDGFR-B in a concentration which is higher than the average concentration of this marker in said tumor centre;

wherein the cells do not express the tumor cell markers CD133 and/or VEGFR-2.

22. An isolated, fixed brain tumor cell composition, wherein said brain tumor cell composition was fixed with paraformaldehyde, wherein at least 60% of the cells comprised therein express the protein and/or the mRNA of the cellular markers CD87 and/or PDGFR-B, wherein the cells comprised therein are derived from the peripheral zone surrounding a tumor centre wherein the cell composition does not comprise cells which are located less than 2 mm away from the surface of the tumor centre and wherein the cells which express the cellular markers CD87 and/or PDGFR-B
- (i) express the cellular marker CD87 in a concentration which is higher than the average concentration of this marker in said tumor centre; and/or
- (ii) express the cellular marker PDGFR-B in a concentration which is higher than the average concentration of this marker in said tumor centre.

23. The isolated brain tumor cell composition of claim 22, wherein the cells further
- (iii) express the cellular marker CD133 in a concentration which is lower than the average concentration of this marker in said tumor centre; and/or
- (iv) express the cellular marker VEGFR-2 in a concentration which is lower than the average concentration of this marker in said tumor centre.

24. The isolated brain tumor cell composition of claim 22, wherein the cells do not express the tumor cell markers CD133 and / or VEGFR-2.

* * * * *

UNITED STATES PATENT AND TRADEMARK OFFICE
CERTIFICATE OF CORRECTION

PATENT NO. : 9,103,819 B2  Page 1 of 1
APPLICATION NO. : 12/867442
DATED : August 11, 2015
INVENTOR(S) : Björn Scheffler et al.

It is certified that error appears in the above-identified patent and that said Letters Patent is hereby corrected as shown below:

Claims

Column 53, Line 61, claim 9, replace "The method according claim 5" with --The method according to claim 5--.

Column 55, Line 34, claim 17, remove "and".

Column 56, Line 34, claim 18, replace "in step (b); or)" with --in step (b); or--.

Signed and Sealed this
Twenty-sixth Day of January, 2016

Michelle K. Lee
*Director of the United States Patent and Trademark Office*

SEQUENCE LISTING

<160> NUMBER OF SEQ ID NOS: 26

<210> SEQ ID NO 1
<211> LENGTH: 865
<212> TYPE: PRT
<213> ORGANISM: homo sapiens

<400> SEQUENCE: 1

```
Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
                35                  40                  45

Ala Gly Pro Ile Gly Ile Leu Phe Glu Leu Val His Ile Phe Leu Tyr
        50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
                100                 105                 110

Cys Val Leu Gly Leu Leu Phe Ile Ile Leu Met Pro Leu Val Gly Tyr
            115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
            195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
                260                 265                 270

Met Asn Ser Thr Leu Lys Ser Leu His Gln Gln Ser Thr Gln Leu Ser
    275                 280                 285

Ser Ser Leu Thr Ser Val Lys Thr Ser Leu Arg Ser Ser Leu Asn Asp
    290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
        355                 360                 365
```

```
Asp Arg Val Gln Arg Gln Thr Thr Val Val Ala Gly Ile Lys Arg
370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
                420                 425                 430

Tyr Trp Trp Leu Gly Gly Leu Val Ile Cys Ser Leu Leu Thr Leu Ile
                435                 440                 445

Val Ile Phe Tyr Tyr Leu Gly Leu Leu Cys Gly Val Cys Gly Tyr Asp
450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
                500                 505                 510

Lys Leu Ile Cys Glu Pro Tyr Thr Ser Lys Glu Leu Phe Arg Val Leu
                515                 520                 525

Asp Thr Pro Tyr Leu Leu Asn Glu Asp Trp Glu Tyr Tyr Leu Ser Gly
                530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
                580                 585                 590

Ser Ile Ser Ser Glu Leu Glu Ser Leu Lys Val Asn Leu Asn Ile Phe
                595                 600                 605

Leu Leu Gly Ala Ala Gly Arg Lys Asn Leu Gln Asp Phe Ala Ala Cys
                610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
                660                 665                 670

Asp Ala Gln Thr Ile Lys Thr Ile His Gln Gln Arg Val Leu Pro Ile
                675                 680                 685

Glu Gln Ser Leu Ser Thr Leu Tyr Gln Ser Val Lys Ile Leu Gln Arg
690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Thr Ser Ser Val Ile Ile
                725                 730                 735

Glu Glu Thr Lys Lys Tyr Gly Arg Thr Ile Ile Gly Tyr Phe Glu His
                740                 745                 750

Tyr Leu Gln Trp Ile Glu Phe Ser Ile Ser Glu Lys Val Ala Ser Cys
                755                 760                 765

Lys Pro Val Ala Thr Ala Leu Asp Thr Ala Val Asp Val Phe Leu Cys
770                 775                 780

Ser Tyr Ile Ile Asp Pro Leu Asn Leu Phe Trp Phe Gly Ile Gly Lys
```

Ala Thr Val Phe Leu Leu Pro Ala Leu Ile Phe Ala Val Lys Leu Ala
             805                 810                 815

Lys Tyr Tyr Arg Arg Met Asp Ser Glu Asp Val Tyr Asp Asp Val Glu
             820                 825                 830

Thr Ile Pro Met Lys Asn Met Glu Asn Gly Asn Asn Gly Tyr His Lys
             835                 840                 845

Asp His Val Tyr Gly Ile His Asn Pro Val Met Thr Ser Pro Ser Gln
         850                 855                 860

His
865

<210> SEQ ID NO 2
<211> LENGTH: 3794
<212> TYPE: DNA
<213> ORGANISM: homo sapiens

<400> SEQUENCE: 2

| | | | | | |
|---|---|---|---|---|---|
| ccaagttcta | cctcatgttt | ggaggatctt | gctagctatg | gccctcgtac | tcggctccct | 60 |
| gttgctgctg | gggctgtgcg | ggaactcctt | ttcaggaggg | cagccttcat | ccacagatgc | 120 |
| tcctaaggct | tggaattatg | aattgcctgc | aacaaattat | gagacccaag | actcccataa | 180 |
| agctggaccc | attggcattc | tctttgaact | agtgcatatc | tttctctatg | tggtacagcc | 240 |
| gcgtgatttc | ccagaagata | cttttgagaaa | attcttacag | aaggcatatg | aatccaaaat | 300 |
| tgattatgac | aagccagaaa | ctgtaatctt | aggtctaaag | attgtctact | atgaagcagg | 360 |
| gattattcta | tgctgtgtcc | tggggctgct | gtttattatt | ctgatgcctc | tggtggggta | 420 |
| tttcttttgt | atgtgtcgtt | gctgtaacaa | atgtggtgga | gaaatgcacc | agcgacagaa | 480 |
| ggaaaatggg | cccttcctga | ggaaatgctt | gcaatctcc | ctgttggtga | tttgtataat | 540 |
| aataagcatt | ggcatcttct | atggttttgt | ggcaaatcac | caggtaagaa | cccggatcaa | 600 |
| aaggagtcgg | aaactggcag | atagcaattt | caaggacttg | cgaactctct | tgaatgaaac | 660 |
| tccagagcaa | atcaaatata | tattggccca | gtacaacact | accaaggaca | aggcgttcac | 720 |
| agatctgaac | agtatcaatt | cagtgctagg | aggcggaatt | cttgaccgac | tgagacccaa | 780 |
| catcatccct | gttcttgatg | agattaagtc | catggcaaca | gcgatcaagg | agaccaaaga | 840 |
| ggcgttggag | aacatgaaca | gcaccttgaa | gagcttgcac | caacaaagta | cacagcttag | 900 |
| cagcagtctg | accagcgtga | aaactagcct | gcggtcatct | ctcaatgacc | ctctgtgctt | 960 |
| ggtgcatcca | tcaagtgaaa | cctgcaacag | catcagattg | tctctaagcc | agctgaatag | 1020 |
| caaccctgaa | ctgaggcagc | ttccacccgt | ggatgcagaa | cttgacaacg | ttaataacgt | 1080 |
| tcttaggaca | gatttggatg | gcctggtcca | acagggctat | caatccctta | atgatatacc | 1140 |
| tgacagagta | caacgccaaa | ccacgactgt | cgtagcaggt | atcaaaaggg | tcttgaattc | 1200 |
| cattggttca | gatatcgaca | atgtaactca | gcgtcttcct | attcaggata | tactctcagc | 1260 |
| attctctgtt | tatgttaata | acactgaaag | ttacatccac | agaaatttac | ctacattgga | 1320 |
| agagtatgat | tcatactggt | ggctgggtgg | cctggtcatc | tgctctctgc | tgaccctcat | 1380 |
| cgtgatttt | tactacctgg | gcttactgtg | tggcgtgtgc | ggctatgaca | ggcatgccac | 1440 |
| cccgaccacc | cgaggctgtg | tctccaacac | cggaggcgtc | ttcctcatgg | ttggagttgg | 1500 |
| attaagtttc | ctctttttgct | ggatattgat | gatcattgtg | gttcttacct | ttgtctttgg | 1560 |
| tgcaaatgtg | gaaaaactga | tctgtgaacc | ttacacgagc | aaggaattat | tccgggtttt | 1620 |

-continued

| | |
|---|---|
| ggatacaccc tacttactaa atgaagactg ggaatactat ctctctggga agctatttaa | 1680 |
| taaatcaaaa atgaagctca cttttgaaca agtttacagt gactgcaaaa aaaatagagg | 1740 |
| cacttacggc actcttcacc tgcagaacag cttcaatatc agtgaacatc tcaacattaa | 1800 |
| tgagcatact ggaagcataa gcagtgaatt ggaaagtctg aaggtaaatc ttaatatctt | 1860 |
| tctgttgggt gcagcaggaa gaaaaaacct tcaggatttt gctgcttgtg aatagacag | 1920 |
| aatgaattat gacagctact tggctcagac tggtaaatcc cccgcaggag tgaatctttt | 1980 |
| atcatttgca tatgatctag aagcaaaagc aaacagtttg cccccaggaa atttgaggaa | 2040 |
| ctccctgaaa agagatgcac aaactattaa aacaattcac cagcaacgag tccttcctat | 2100 |
| agaacaatca ctgagcactc tataccaaag cgtcaagata cttcaacgca cagggaatgg | 2160 |
| attgttggag agagtaacta ggattctagc ttctctggat tttgctcaga acttcatcac | 2220 |
| aaacaatact tcctctgtta ttattgagga aactaagaag tatgggagaa caataatagg | 2280 |
| atattttgaa cattatctgc agtggatcga gttctctatc agtgagaaag tggcatcgtg | 2340 |
| caaacctgtg gccaccgctc tagatactgc tgttgatgtc tttctgtgta gctacattat | 2400 |
| cgaccccttg aatttgtttt ggtttggcat aggaaaagct actgtatttt tacttccggc | 2460 |
| tctaatttt gcggtaaaac tggctaagta ctatcgtcga atggattcgg aggacgtgta | 2520 |
| cgatgatgtt gaactatac ccatgaaaaa tatggaaaat ggtaataatg gttatcataa | 2580 |
| agatcatgta tatggtattc acaatcctgt tatgacaagc ccatcacaac attgatagct | 2640 |
| gatgttgaaa ctgcttgagc atcaggatac tcaaagtgga aaggatcaca gattttggt | 2700 |
| agtttctggg tctacaagga cttcccaaat ccaggagcaa cgccagtggc aacgtagtga | 2760 |
| ctcaggcggg caccaaggca acggcaccat tggtctctgg gtagtgcttt aagaatgaac | 2820 |
| acaatcacgt tatagtccat ggtccatcac tattcaagga tgactccctc ccttcctgtc | 2880 |
| tattttgtt ttttacttt ttacactgag tttctattta gacactacaa catatggggt | 2940 |
| gtttgttccc attggatgca tttctatcaa aactctatca aatgtgatgg ctagattcta | 3000 |
| acatattgcc atgtgtggag tgtgctgaac acacaccagt ttacaggaaa gatgcatttt | 3060 |
| gtgtacagta aacggtgtat ataccttttg ttaccacaga gttttttaaa caaatgagta | 3120 |
| ttataggact ttcttctaaa tgagctaaat aagtcaccat tgacttcttg gtgctgttga | 3180 |
| aaataatcca ttttcactaa aagtgtgtga aacctacagc atattcttca cgcagagatt | 3240 |
| ttcatctatt atactttatc aaagattggc catgttccac ttggaaatgg catgcaaaag | 3300 |
| ccatcataga gaaacctgcg taactccatc tgacaaattc aaaagagaga gagagatctt | 3360 |
| gagagagaaa tgctgttcgt tcaaaagtgg agttgtttta acagatgcca attacggtgt | 3420 |
| acagtttaac agagttttct gttgcattag gataaacatt aattggagtg cagctaacat | 3480 |
| gagtatcatc agactagtat caagtgttct aaaatgaaat atgagaagat cctgtcacaa | 3540 |
| ttcttagatc tggtgtccag catggatgaa acctttgagt ttggtcccta aatttgcatg | 3600 |
| aaagcacaag gtaaatattc atttgcttca ggagtttcat gttggatctg tcattatcaa | 3660 |
| aagtgatcag caatgaagaa ctggtcggac aaaatttaac gttgatgtaa tggaattcca | 3720 |
| gatgtaggca ttccccccag gtcttttcat gtgcagattg cagttctgat tcatttgaat | 3780 |
| aaaaaggaac ttgg | 3794 |

<210> SEQ ID NO 3
<211> LENGTH: 335
<212> TYPE: PRT
<213> ORGANISM: homo sapiens

<400> SEQUENCE: 3

```
Met Gly His Pro Pro Leu Leu Pro Leu Leu Leu Leu His Thr Cys
1               5                   10                  15

Val Pro Ala Ser Trp Gly Leu Arg Cys Met Gln Cys Lys Thr Asn Gly
            20                  25                  30

Asp Cys Arg Val Glu Glu Cys Ala Leu Gly Gln Asp Leu Cys Arg Thr
        35                  40                  45

Thr Ile Val Arg Leu Trp Glu Gly Glu Glu Glu Leu Glu Val Glu
    50                  55                  60

Lys Ser Cys Thr His Ser Glu Lys Thr Asn Arg Thr Leu Ser Tyr Arg
65                  70                  75                  80

Thr Gly Leu Lys Ile Thr Ser Leu Thr Glu Val Val Cys Gly Leu Asp
                85                  90                  95

Leu Cys Asn Gln Gly Asn Ser Gly Arg Ala Val Thr Tyr Ser Arg Ser
            100                 105                 110

Arg Tyr Leu Glu Cys Ile Ser Cys Gly Ser Ser Asp Met Ser Cys Glu
        115                 120                 125

Arg Gly Arg His Gln Ser Leu Gln Cys Arg Ser Pro Glu Glu Gln Cys
    130                 135                 140

Leu Asp Val Val Thr His Trp Ile Gln Glu Gly Glu Glu Gly Arg Pro
145                 150                 155                 160

Lys Asp Arg His Leu Arg Gly Cys Gly Tyr Leu Pro Gly Cys Pro
                165                 170                 175

Gly Ser Asn Gly Phe His Asn Asn Asp Thr Phe His Phe Leu Lys Cys
            180                 185                 190

Cys Asn Thr Thr Lys Cys Asn Glu Gly Pro Ile Leu Glu Leu Glu Asn
        195                 200                 205

Leu Pro Gln Asn Gly Arg Gln Cys Tyr Ser Cys Lys Gly Asn Ser Thr
    210                 215                 220

His Gly Cys Ser Ser Glu Glu Thr Phe Leu Ile Asp Cys Arg Gly Pro
225                 230                 235                 240

Met Asn Gln Cys Leu Val Ala Thr Gly Thr His Glu Pro Lys Asn Gln
                245                 250                 255

Ser Tyr Met Val Arg Gly Cys Ala Thr Ala Ser Met Cys Gln His Ala
            260                 265                 270

His Leu Gly Asp Ala Phe Ser Met Asn His Ile Asp Val Ser Cys Cys
        275                 280                 285

Thr Lys Ser Gly Cys Asn His Pro Asp Leu Asp Val Gln Tyr Arg Ser
    290                 295                 300

Gly Ala Ala Pro Gln Pro Gly Pro Ala His Leu Ser Leu Thr Ile Thr
305                 310                 315                 320

Leu Leu Met Thr Ala Arg Leu Trp Gly Gly Thr Leu Leu Trp Thr
                325                 330                 335
```

<210> SEQ ID NO 4
<211> LENGTH: 1548
<212> TYPE: DNA
<213> ORGANISM: homo sapiens

<400> SEQUENCE: 4

```
cagggccgag ccagcccctt caccaccagc cggccgcgcc ccgggaaggg aagtttgtgg    60
cggaggaggt tcgtacggga ggagggggag gcgcccacgc atctgggggct gactcgctct   120 ttcgcaaaac gtctgggagg agtccctggg gccacaaaac tgcctccttc ctgaggccag   180
```

```
aaggagagaa gacgtgcagg gaccccgcgc acaggagctg ccctcgcgac atgggtcacc      240
cgccgctgct gccgctgctg ctgctgctcc acacctgcgt cccagcctct tggggcctgc      300
ggtgcatgca gtgtaagacc aacggggatt gccgtgtgga agagtgcgcc ctgggacagg      360
acctctgcag gaccacgatc gtgcgcttgt gggaagaagg agaagagctg gagctggtgg      420
agaaaagctg tacccactca gagaagacca acaggaccct gagctatcgg actggcttga      480
agatcaccag ccttaccgag gttgtgtgtg ggttagactt gtgcaaccag gcaactctg       540 gccgggctgt cacctattcc cgaagccgtt acctcgaatg catttcctgt ggctcatcag      600
acatgagctg tgagaggggc cggcaccaga gcctgcagtg ccgcagccct gaagaacagt      660
gcctggatgt ggtgacccac tggatccagg aaggtgaaga agggcgtcca aaggatgacc      720
gccacctccg tggctgtggc taccttcccg gctgcccggg ctccaatggt ttccacaaca      780
acgacacctt ccacttcctg aaatgctgca acaccaccaa atgcaacgag ggcccaatcc      840
tggagcttga aaatctgccg cagaatggcc gccagtgtta cagctgcaag gggaacagca      900
cccatggatg ctcctctgaa gagactttcc tcattgactg ccgaggcccc atgaatcaat      960
gtctggtagc caccggcact cacgaaccga aaaaccaaag ctatatggta agaggctgtg     1020
caaccgcctc aatgtgccaa catgcccacc tgggtgacgc cttcagcatg aaccacattg     1080
atgtctcctg ctgtactaaa agtggctgta accacccaga cctggatgtc cagtaccgca     1140
gtggggctgc tcctcagcct ggccctgccc atctcagcct caccatcacc ctgctaatga     1200
ctgccagact gtggggaggc actctcctct ggacctaaac ctgaaatccc cctctctgcc     1260
ctggctggat ccgggggacc cctttgccct tccctcggct cccagcccta cagacttgct     1320
gtgtgacctc aggccagtgt gccgacctct ctgggcctca gttttcccag ctatgaaaac     1380
agctatctca caaagttgtg tgaagcagaa gagaaaagct ggaggaaggc cgtgggccaa     1440
tgggagagct cttgttatta ttaatattgt tgccgctgtt gtgttgttgt tattaattaa     1500
tattcatatt atttatttta tacttacata aagattttgt accagtgg                  1548

<210> SEQ ID NO 5
<211> LENGTH: 20
<212> TYPE: DNA
<213> ORGANISM: Artificial Sequence
<220> FEATURE:
<223> OTHER INFORMATION: CD44 Forward Primer

<400> SEQUENCE: 5
ccagctaagg acatttccca                                                    20

<210> SEQ ID NO 6
<211> LENGTH: 20
<212> TYPE: DNA
<213> ORGANISM: Artificial Sequence
<220> FEATURE:
<223> OTHER INFORMATION: CD44 Reverse Primer

<400> SEQUENCE: 6
actagtacac cccaaccccc                                                    20

<210> SEQ ID NO 7
<211> LENGTH: 26
<212> TYPE: DNA
<213> ORGANISM: Artificial Sequence
<220> FEATURE:
<223> OTHER INFORMATION: L1CAM Forward Primer
```

```
<400> SEQUENCE: 7
gactacgaga tccacttgtt taagga                                          26

<210> SEQ ID NO 8
<211> LENGTH: 20
<212> TYPE: DNA
<213> ORGANISM: Artificial Sequence
<220> FEATURE:
<223> OTHER INFORMATION: L1CAM Reverse Primer

<400> SEQUENCE: 8
ctcacaaagc cgatgaacca                                                 20

<210> SEQ ID NO 9
<211> LENGTH: 20
<212> TYPE: DNA
<213> ORGANISM: Artificial Sequence
<220> FEATURE:
<223> OTHER INFORMATION: Nestin Forward Primer

<400> SEQUENCE: 9
gccctgacca ctccagttta                                                 20

<210> SEQ ID NO 10
<211> LENGTH: 20
<212> TYPE: DNA
<213> ORGANISM: Artificial Sequence
<220> FEATURE:
<223> OTHER INFORMATION: Nestin Reverse Primer

<400> SEQUENCE: 10
ggagtcctgg atttccttcc                                                 20

<210> SEQ ID NO 11
<211> LENGTH: 20
<212> TYPE: DNA
<213> ORGANISM: Artificial Sequence
<220> FEATURE:
<223> OTHER INFORMATION: PDGFR-A Forward Primer

<400> SEQUENCE: 11
tctatgatcg tccagcctca                                                 20

<210> SEQ ID NO 12
<211> LENGTH: 20
<212> TYPE: DNA
<213> ORGANISM: Artificial Sequence
<220> FEATURE:
<223> OTHER INFORMATION: PDGFR-A Reverse Primer

<400> SEQUENCE: 12
ttcctcgggc aacttgatag                                                 20

<210> SEQ ID NO 13
<211> LENGTH: 18
<212> TYPE: DNA
<213> ORGANISM: Artificial Sequence
<220> FEATURE:
<223> OTHER INFORMATION: PDGFR-B Forward Primer

<400> SEQUENCE: 13
catcgtggtg ccacactc                                                   18

<210> SEQ ID NO 14
<211> LENGTH: 20
```

```
<212> TYPE: DNA
<213> ORGANISM: Artificial Sequence
<220> FEATURE:
<223> OTHER INFORMATION: PDGFR-B Reverse Primer

<400> SEQUENCE: 14
ggatctcgta acgtggcttc                                          20

<210> SEQ ID NO 15
<211> LENGTH: 24
<212> TYPE: DNA
<213> ORGANISM: Artificial Sequence
<220> FEATURE:
<223> OTHER INFORMATION: Sox-2 Forward Primer

<400> SEQUENCE: 15
gtatcaggag ttgtcaaggc agag                                     24

<210> SEQ ID NO 16
<211> LENGTH: 25
<212> TYPE: DNA
<213> ORGANISM: Artificial Sequence
<220> FEATURE:
<223> OTHER INFORMATION: Sox-2 Reverse Primer

<400> SEQUENCE: 16
tcctagtctt aaagaggcag caaac                                    25

<210> SEQ ID NO 17
<211> LENGTH: 20
<212> TYPE: DNA
<213> ORGANISM: Artificial Sequence
<220> FEATURE:
<223> OTHER INFORMATION: TGFB-2 Forward Primer

<400> SEQUENCE: 17
ttgacgtctc agcaatggag                                          20

<210> SEQ ID NO 18
<211> LENGTH: 20
<212> TYPE: DNA
<213> ORGANISM: Artificial Sequence
<220> FEATURE:
<223> OTHER INFORMATION: TGFB-2 Reverse Primer

<400> SEQUENCE: 18
tcgccttctg ctcttgtttt                                          20

<210> SEQ ID NO 19
<211> LENGTH: 20
<212> TYPE: DNA
<213> ORGANISM: Artificial Sequence
<220> FEATURE:
<223> OTHER INFORMATION: TGFBR-1 Forward Primer

<400> SEQUENCE: 19
gcaaaggtcg atttggagaa                                          20

<210> SEQ ID NO 20
<211> LENGTH: 20
<212> TYPE: DNA
<213> ORGANISM: Artificial Sequence
<220> FEATURE:
<223> OTHER INFORMATION: TGFBR-1 Reverse Primer

<400> SEQUENCE: 20
```

```
ctgacaccaa ccagagctga                                                   20
```

```
<210> SEQ ID NO 21
<211> LENGTH: 24
<212> TYPE: DNA
<213> ORGANISM: Artificial Sequence
<220> FEATURE:
<223> OTHER INFORMATION: VEGF-A Forward Primer

<400> SEQUENCE: 21
ccctgatgag atcgagtaca tctt                                              24
```

```
<210> SEQ ID NO 22
<211> LENGTH: 18
<212> TYPE: DNA
<213> ORGANISM: Artificial Sequence
<220> FEATURE:
<223> OTHER INFORMATION: VEGF-A Reverse Primer

<400> SEQUENCE: 22
accgcctcgg cttgtcac                                                     18
```

```
<210> SEQ ID NO 23
<211> LENGTH: 20
<212> TYPE: DNA
<213> ORGANISM: Artificial Sequence
<220> FEATURE:
<223> OTHER INFORMATION: VEGFR-2 Forward Primer

<400> SEQUENCE: 23
cagcatcacc agtagccaga                                                   20
```

```
<210> SEQ ID NO 24
<211> LENGTH: 20
<212> TYPE: DNA
<213> ORGANISM: Artificial Sequence
<220> FEATURE:
<223> OTHER INFORMATION: VEGFR-2 Reverse Primer

<400> SEQUENCE: 24
gtggatacac tttcgcgatg                                                   20
```

```
<210> SEQ ID NO 25
<211> LENGTH: 18
<212> TYPE: DNA
<213> ORGANISM: Artificial Sequence
<220> FEATURE:
<223> OTHER INFORMATION: 18S Forward Primer

<400> SEQUENCE: 25
ttcttggacc ggcgcaag                                                     18
```

```
<210> SEQ ID NO 26
<211> LENGTH: 17
<212> TYPE: DNA
<213> ORGANISM: Artificial Sequence
<220> FEATURE:
<223> OTHER INFORMATION: 18S Reverse Primer

<400> SEQUENCE: 26
gccgcatcgc cggtcgg                                                      17
```